United States Patent
Mizuno et al.

(10) Patent No.: US 10,119,028 B2
(45) Date of Patent: Nov. 6, 2018

(54) INFRARED-SENSITIVE COLOR DEVELOPING COMPOSITION, LITHOGRAPHIC PRINTING PLATE PRECURSOR, PLATE MAKING METHOD FOR LITHOGRAPHIC PRINTING PLATE, AND INFRARED-SENSITIVE COLOR DEVELOPER

(71) Applicant: FUJIFILM Corporation, Tokyo (JP)

(72) Inventors: Akio Mizuno, Shizuoka (JP); Shota Suzuki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 125 days.

(21) Appl. No.: 15/203,870

(22) Filed: Jul. 7, 2016

(65) Prior Publication Data

US 2016/0326372 A1    Nov. 10, 2016

Related U.S. Application Data

(63) Continuation of application No. PCT/JP2015/052670, filed on Jan. 30, 2015.

(30) Foreign Application Priority Data

Jan. 31, 2014  (JP) .................................. 2014-016671

(51) Int. Cl.
| | | |
|---|---|---|
| G03F 7/32 | (2006.01) | |
| C09B 23/10 | (2006.01) | |
| C07D 413/14 | (2006.01) | |
| C07D 403/14 | (2006.01) | |
| C07D 417/14 | (2006.01) | |
| C07D 209/14 | (2006.01) | |
| C07D 277/64 | (2006.01) | |
| C08F 20/36 | (2006.01) | |
| C09B 23/00 | (2006.01) | |
| C09K 9/02 | (2006.01) | |
| B41C 1/10 | (2006.01) | |
| C09B 23/01 | (2006.01) | |
| B41M 5/28 | (2006.01) | |
| B41M 5/333 | (2006.01) | |

(52) U.S. Cl.
CPC ............. *C09B 23/107* (2013.01); *B41C 1/10* (2013.01); *B41C 1/1008* (2013.01); *B41C 1/1016* (2013.01); *C07D 209/14* (2013.01); *C07D 277/64* (2013.01); *C07D 403/14* (2013.01); *C07D 413/14* (2013.01); *C07D 417/14* (2013.01); *C08F 20/36* (2013.01); *C09B 23/00* (2013.01); *C09B 23/0066* (2013.01); *C09K 9/02* (2013.01); *B41C 2201/04* (2013.01); *B41C 2201/10* (2013.01); *B41C 2210/04* (2013.01); *B41C 2210/22* (2013.01); *B41M 5/286* (2013.01); *B41M 5/333* (2013.01)

(58) Field of Classification Search
CPC ....................................................... G03F 7/00
See application file for complete search history.

(56) References Cited

U.S. PATENT DOCUMENTS

2002/0182530 A1\* 12/2002 Takashima .............. G03F 7/002
430/138

FOREIGN PATENT DOCUMENTS

JP    2013/199089 A    10/2013

OTHER PUBLICATIONS

Written Opinion for PCT/JP2015/052670 dated Mar. 3, 2015.

\* cited by examiner

*Primary Examiner* — Chanceity N Robinson
(74) *Attorney, Agent, or Firm* — Sughrue Mion, PLLC

(57) ABSTRACT

An infrared-sensitive color developing composition develops colors in a high density with an infrared exposure and does not significantly discolor when aged. A lithographic printing plate precursor which has extremely excellent plate-inspecting properties and favorable storage stability and is capable of maintaining favorable color-developing properties is provided, as is a plate making method for a lithographic printing plate in which the lithographic printing plate precursor is used. A new compound that can be preferably used as an infrared-sensitive color developer is also provided. An infrared-sensitive color developing composition of the invention includes a compound represented by Formula (1) (Component A). In addition, the compound in the present invention is represented by Formula (1).

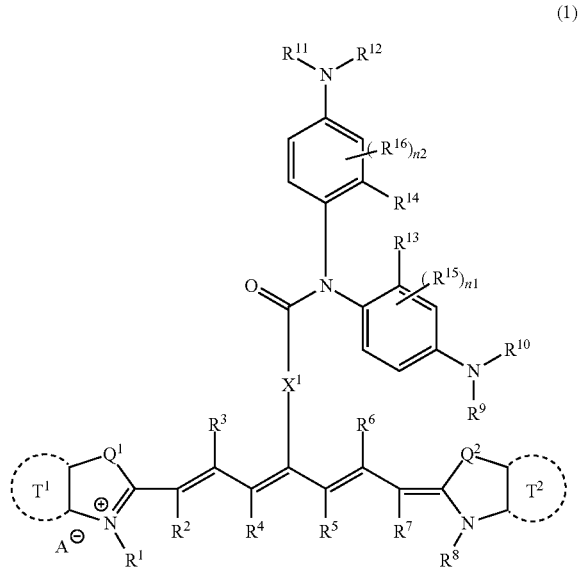

(1)

14 Claims, No Drawings

INFRARED-SENSITIVE COLOR DEVELOPING COMPOSITION, LITHOGRAPHIC PRINTING PLATE PRECURSOR, PLATE MAKING METHOD FOR LITHOGRAPHIC PRINTING PLATE, AND INFRARED-SENSITIVE COLOR DEVELOPER

CROSS-REFERENCE TO RELATED APPLICATIONS

This application is a Continuation of PCT International Application No. PCT/JP2015/052670 filed on Jan. 30, 2015, which claims priority under 35 U.S.C. § 119(a) to Japanese Patent Application No. 2014-016671 filed on Jan. 31, 2014. The contents of these applications are incorporated herein by reference in their entirety.

BACKGROUND OF THE INVENTION

1. Field of the Invention

The present invention relates to an infrared-sensitive color developing composition, a lithographic printing plate precursor, a plate making method for a lithographic printing plate, and a new compound that can be preferably used as an infrared-sensitive color developer.

2. Description of the Related Art

At the moment, lithographic printing plates are produced using computer to plate (CTP) technologies. That is, lithographic printing plates are produced by directly scanning, exposing, and developing lithographic printing plate precursors using lasers or laser diodes without using lith films.

In response to the above-described technological advances, regarding lithographic printing plate precursors, there is a changing demand for improvement in image-recording characteristics, printing characteristics, physical characteristics, and the like in accordance with the CTP technologies. In addition, due to increasing interest in the global environment, regarding lithographic printing plate precursors, there is another attention-gathering environmental demand for good treatments of waste liquid used for wet processes such as a development process.

Regarding the above-described environmental demand, there have been attempts to facilitate development or plate-making or to remove processes. As one of easy plate making methods, a method called "on-machine development" is carried out. That is, in the method, after the exposure of lithographic printing plate precursors, development of the related art is not carried out, and instead, the lithographic printing plate precursors are mounted on printers, and unnecessary portions in image-recording layers are removed at the initial phase of an ordinary printing step.

In on-machine development-type or process-less (development-less)-type lithographic printing plate precursors on which no development process is carried out, there are no images on the printing plates in a phase of mounting the printing plates on printers, and thus plate inspection is not possible. Particularly, whether or not it is possible to determine if register marks, which serve as indicators for registration in polychromatic printing, are drawn is critical in printing operations. Therefore, for on-machine development-type or process-less (development-less)-type lithographic printing plate precursors, there is a demand for means for checking exposed images, that is, the generation of so-called print-out images in which exposed regions develop or do not develop colors. Furthermore, from the viewpoint of improving workability, there is another demand that exposed regions which develop or do not develop colors remain unchanged regardless of the elapsing of time and maintain a state of developing or not developing colors.

In addition, as lithographic printing plate precursors of the related art, lithographic printing plate precursors described in JP2013-199089A are known.

SUMMARY OF THE INVENTION

An object of the present invention is to provide an infrared-sensitive color developing composition which develops colors in a high density by means of infrared exposure and does not significantly discolor when aged.

Another object of the present invention is to provide a lithographic printing plate precursor which has extremely excellent plate-inspecting properties and favorable storage stability and is capable of maintaining favorable color-developing properties and a plate making method for a lithographic printing plate in which the lithographic printing plate precursor is used.

Still another object of the present invention is to provide a new compound that can be preferably used as an infrared-sensitive color developer.

The above-described objects have been achieved using means described in <1>, <7>, <11>, or <12> below. Preferred embodiments <2> to <6>, <8> to <10>, <13> and <14> will also be described together.

<1> An infrared-sensitive color developing composition comprising a compound represented by Formula (1) (Component A).

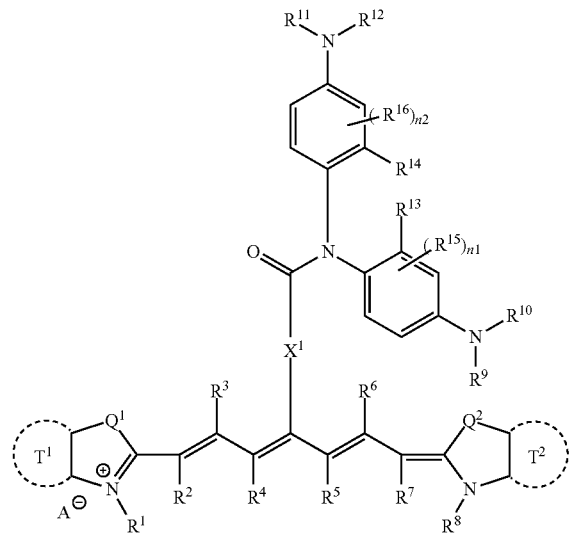

(1)

In Formula (1), each of $R^1$ and $R^8$ independently represents an alkyl group, each of $R^2$, $R^3$, $R^4$, $R^5$, $R^6$, and $R^7$ independently represents a hydrogen atom or an alkyl group, $R^4$ and $R^5$ may be linked together and thus form a ring, each of $Q^1$ and $Q^2$ independently represents —$NR^0$—, —S—, —O—, or a dialkylmethylene group, $R^0$ represents a hydrogen atom, an alkyl group, or an aryl group, each of $T^1$ and $T^2$ independently represents an aromatic ring or a heterocyclic aromatic ring, $X^1$ represents a divalent linking group, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom or a monovalent substituent, $R^{13}$ and $R^{14}$ may be bonded together and thus form a ring, each of $R^{15}$ and $R^{16}$ independently represents a monovalent substituent, and each of n1 and n2 independently represents an integer of 0 to 3.

<2> The infrared-sensitive color developing composition according to <1>, in which the compound represented by Formula (1) is a compound represented by Formula (2) below,

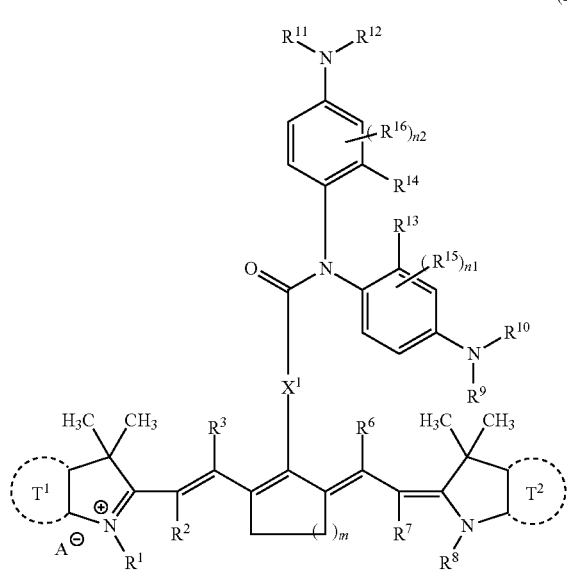

(2)

In Formula (2), each of $R^1$ and $R^8$ independently represents an alkyl group, each of $R^2$, $R^3$, $R^6$, and $R^7$ independently represents a hydrogen atom or an alkyl group, each of $T^1$ and $T^2$ independently represents an aromatic ring or a heterocyclic aromatic ring, $X^1$ represents a group formed by bonding one or more of —O—, —S—, and/or a urethane bond to one or more of divalent hydrocarbon groups, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom, an alkyl group, a halogen atom, $OR^{17}$, $NR^{18}R^{19}$, or $SR^{20}$, $R^{13}$ and $R^{14}$ may form a ring bonded by an alkylene group, —O—, —$NR^{21}$—, —S—, or a group made of a combination of two or more thereof, each of $R^{15}$ and $R^{16}$ independently represents an alkyl group, a halogen atom, $OR^{17}$, $NR^{18}R^{19}$, or $SR^{20}$, each of $R^{17}$, $R^{18}$, $R^{19}$, and $R^{20}$ independently represents an alkyl group or an aryl group, $R^{21}$ represents a hydrogen atom, an alkyl group, or an aryl group, each of n1 and n2 independently represents an integer of 0 to 3, and m represents 1 or 2.

<3> The infrared-sensitive color developing composition according to <1> or <2>, in which the compound represented by Formula (1) is a compound represented by Formula (3) below.

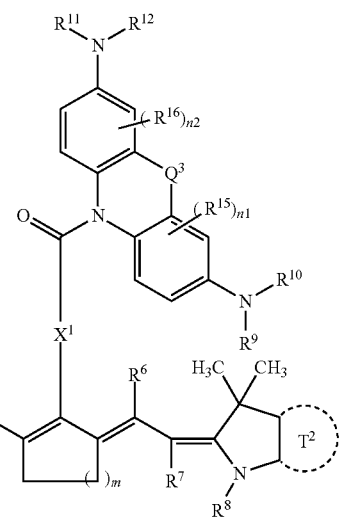

(3)

In Formula (3), each of $R^1$ and $R^8$ independently represents an alkyl group, each of $R^2$, $R^3$, $R^6$, and $R^7$ independently represents a hydrogen atom or an alkyl group, each of $T^1$ and $T^2$ independently represents an aromatic ring or a heterocyclic aromatic ring, $X^1$ represents a group formed by bonding one or more of —O—, —S—, and/or a urethane bond to one or more of divalent hydrocarbon groups, $A^-$ represents a counter anion, each of $R^9$, $R^{10}$, $R^{11}$, and $R^{12}$ independently represents an alkyl group or an aryl group, each of $R^{15}$ and $R^{16}$ independently represents a hydrogen atom, an alkyl group, a halogen atom, $OR^{17}$, $NR^{18}R^{19}$, or $SR^{20}$, each of $R^{17}$, $R^{18}$, $R^{19}$, and $R^{20}$ independently represents an alkyl group or an aryl group, each of n1 and n2 independently represents an integer of 0 to 3, m represents 1 or 2, $Q^3$ represents —O—, —$NR^{22}$— or —S—, and $R^{22}$ represents an alkyl group or an aryl group.

<4> The infrared-sensitive color developing composition according to any one of <1> to <3>, further comprising: a binder polymer (Component B).

<5> The infrared-sensitive color developing composition according to any one of <1> to <4>, further comprising: a polymerization initiator (Component C).

<6> The infrared-sensitive color developing composition according to any one of <1> to <5>, further comprising: a polymerizable compound (Component D).

<7> A lithographic printing plate precursor comprising on a support: an image-recording layer including a compound represented by Formula (1) (Component A); a binder polymer (Component B); a polymerization initiator (Component C); and a polymerizable compound (Component D).

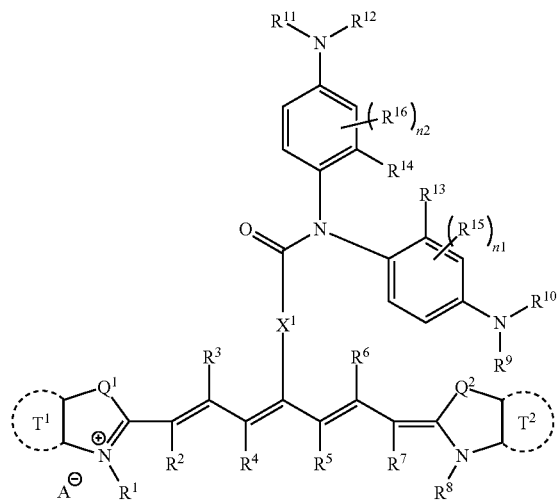

(1)

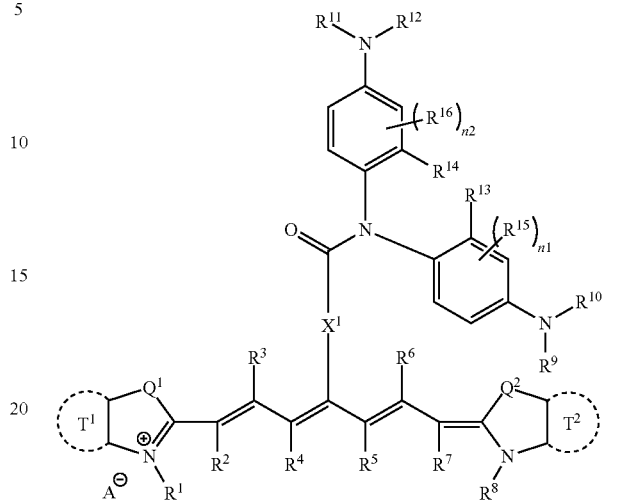

(1)

In Formula (1), each of $R^1$ and $R^8$ independently represents an alkyl group, each of $R^2$, $R^3$, $R^4$, $R^5$, $R^6$, and $R^7$ independently represents a hydrogen atom or an alkyl group, $R^4$ and $R^5$ may be linked together and thus form a ring, each of $Q^1$ and $Q^2$ independently represents —$NR^0$—, —S—, —O—, or a dialkylmethylene group, $R^0$ represents a hydrogen atom, an alkyl group, or an aryl group, each of $T^1$ and $T^2$ independently represents an aromatic ring or a heterocyclic aromatic ring, $X^1$ represents a divalent linking group, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom or a monovalent substituent, $R^{13}$ and $R^{14}$ may be bonded together and thus form a ring, each of $R^{15}$ and $R^{16}$ independently represents a monovalent substituent, and each of n1 and n2 independently represents an integer of 0 to 3.

<8> The lithographic printing plate precursor according to <7>, in which the image-recording layer further contains polymer particles.

<9> The lithographic printing plate precursor according to <7> or <8>, comprising: a protective layer on the image-recording layer.

<10> The lithographic printing plate precursor according to <9>, in which the protective layer contains an inorganic lamellar compound.

<11> A plate making method for a lithographic printing plate, comprising: a preparation step of preparing the lithographic printing plate precursor according to any one of <7> to <10>; an exposure step of exposing the lithographic printing plate precursor in an image pattern; and an on-machine development process step of removing non-image portions by supplying printing ink and dampening water to the lithographic printing plate precursor that has been exposed in an image pattern on a printer.

<12> A compound represented by Formula (1).

In Formula (1), each of $R^1$ and $R^8$ independently represents an alkyl group, each of $R^2$, $R^3$, $R^4$, $R^5$, $R^6$, and $R^7$ independently represents a hydrogen atom or an alkyl group, $R^4$ and $R^5$ may be linked together and thus form a ring, each of $Q^1$ and $Q^2$ independently represents —$NR^0$—, —S—, —O—, or a dialkylmethylene group, $R^0$ represents a hydrogen atom, an alkyl group, or an aryl group, each of $T^1$ and $T^2$ independently represents an aromatic ring or a heterocyclic aromatic ring, $X^1$ represents a divalent linking group, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom or a monovalent substituent, $R^{13}$ and $R^{14}$ may be bonded together and thus form a ring, each of $R^{15}$ and $R^{16}$ independently represents a monovalent substituent, and each of n1 and n2 independently represents an integer of 0 to 3.

<13> The compound according to <12>, in which each of $R^1$, $R^8$, $R^9$, $R^{10}$, $R^{11}$, and $R^{12}$ is independently an alkyl group, and $R^2$, $R^3$, $R^6$, and $R^7$ are hydrogen atoms.

<14> The compound according to <12> or <13> which is an infrared-sensitive color developer.

According to the present invention, it is possible to provide an infrared-sensitive color developing composition which develops colors in a high density by means of infrared exposure and does not significantly discolor when aged.

In addition, according to the present invention, it is possible to provide a lithographic printing plate precursor which has extremely excellent plate-inspecting properties and favorable storage stability and is capable of maintaining favorable color-developing properties and a plate making method for a lithographic printing plate in which the lithographic printing plate precursor is used.

Furthermore, according to the present invention, it is possible to provide a new compound that can be preferably used as an infrared-sensitive color developer.

DESCRIPTION OF THE PREFERRED EMBODIMENTS

Hereinafter, the present invention will be described in detail.

Meanwhile, in the present specification, an expression "xx to yy" represents a numerical range including xx and yy. In addition, "the compound represented by Formula (1) (Component A)" will also be referred to as "Component A" or the like.

"(Meth)acrylates" and the like represent "acrylates and/or methacrylates" and the like, which shall apply below.

In addition, in the present invention, "% by mass" and "% by weight" have the same meaning, and "parts by mass" and "parts by weight" have the same meaning.

In addition, in the present invention, combinations of preferred embodiments are also preferred.

In the present specification, regarding the expression of groups in compounds represented by formulae, in a case in which there are no descriptions of whether or not the groups are substituted or not substituted and the groups are capable of further having a substituent, unless particularly otherwise regulated, the groups may be not only unsubstituted groups but also groups having a substituent. For example, in a formula, when there is a description that "R represents an alkyl group, an aryl group, or a heterocyclic group", it means that "R represents an unsubstituted alkyl group, a substituted alkyl group, an unsubstituted aryl group, a substituted aryl group, an unsubstituted heterocyclic group, or a substituted heterocyclic group".

(Infrared-Sensitive Color Developing Composition)

An infrared-sensitive color developing composition of the present invention includes a compound represented by Formula (1) (Component A).

In addition, the infrared-sensitive color developing composition of the present invention can be preferably used for the production of image-recording layers in lithographic printing plate precursors.

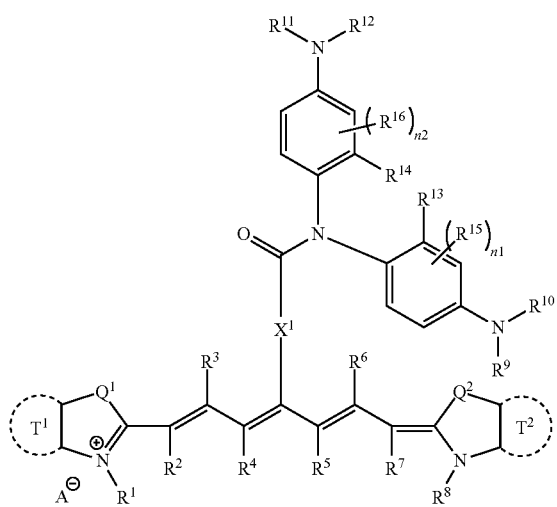

(1)

In Formula (1), each of $R^1$ and $R^8$ independently represents an alkyl group, each of $R^2$, $R^3$, $R^4$, $R^5$, $R^6$, and $R^7$ independently represents a hydrogen atom or an alkyl group, $R^4$ and $R^5$ may be linked together and thus form a ring, each of $Q^1$ and $Q^2$ independently represents —$NR^0$—, —S—, —O—, or a dialkylmethylene group, $R^0$ represents a hydrogen atom, an alkyl group, or an aryl group, each of $T^1$ and $T^2$ independently represents an aromatic ring or a heterocyclic aromatic ring, $X^1$ represents a divalent linking group, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom or a monovalent substituent, $R^{13}$ and $R^{14}$ may be bonded together and thus form a ring, each of $R^{15}$ and $R^{16}$ independently represents a monovalent substituent, and each of n1 and n2 independently represents an integer of 0 to 3.

Compound Represented by Formula (1) (Component A)

The compound represented by Formula (1) (Component A) is a compound which is decomposed by exposure to infrared rays and generates color-developing decomposed matters.

In the present invention, a matter developing colors means that, before exposure, the matter barely absorbs rays in the visible light range (400 nm to 760 nm); however, after exposure, the matter is strongly colored or absorbs rays with longer wavelengths and thus absorbs rays in the visible light range.

The detailed color-developing mechanism of the compound represented by Formula (1) is not clear, but the present inventors and the like assume that, since a structure having a conjugated chain in which $R^1$ to $R^8$ and the like bond to each other has a strong electron-accepting function, the compound represented by Formula (1) is excited by exposure to infrared rays, electrons migrate from a structure having an N,N-bis(p-aminoaryl)amide structure to the structure having a conjugated chain in which $R^1$ to $R^8$ and the like bond to each other, and the N,N-bis(p-aminoaryl)amide structure is one-electron-oxidized in the molecule, whereby a decomposition reaction is caused, and a decomposed matter having a bis(p-aminoaryl)amine cation generated from the decomposition of the N,N-bis(p-aminoaryl)amide structure or a cation having a structure similar thereto develops colors.

In the compound represented by Formula (1), the electron migration efficiency is improved by linking a structure having a conjugated chain that absorbs infrared rays and the N,N-bis(p-aminoaryl)amide structure which decomposes and develops colors, and thus even a small amount of the compound imparts sufficient color-developing properties.

In Formula (1), each of $R^1$ and $R^8$ independently represents an alkyl group which may have a substituent, is preferably an alkyl group having 1 to 20 carbon atoms, more preferably an alkyl group having 1 to 10 carbon atoms, and most preferably an alkyl group having 1 to 4 carbon atoms.

Specific examples thereof include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a hexadecyl group, an octadecyl group, an eicosyl group, an isopropyl group, an isobutyl group, an s-butyl, a t-butyl group, an isopentyl group, a neopentyl group, a 1-methylbutyl group, an isohexyl group, a 2-ethylhexyl group, a 2-methylhexyl group, a cyclohexyl group, a cyclopentyl group, and a 2-norbornyl group.

Among these alkyl groups, a methyl group, an ethyl group, and a propyl group are particularly preferred.

Regarding substituents on these alkyl groups, examples of preferred substituents include alkoxy groups having 12 or less carbon atoms, aryloxy groups having 12 or less carbon atoms, and sulfo groups.

In addition, from the viewpoint of synthesis, $R^1$ and $R^8$ are preferably the same groups.

Among these, each of $R^1$ and $R^8$ is independently preferably an alkyl group having 1 to 10 carbon atoms or an alkoxy alkyl group having 3 to 10 carbon atoms, and more preferably an alkyl group having 1 to 4 carbon atoms or an alkoxy alkyl group having 3 or 4 carbon atoms.

In Formula (1), preferred aspects of the alkyl group represented by $R^2$, $R^3$, $R^4$, $R^5$, $R^6$, or $R^7$ are identical to the preferred aspects of that in a case in which $R^1$ or $R^8$ represents an alkyl group.

From the viewpoint of synthesis and the electron-accepting function, $R^4$ and $R^5$ are preferably linked together and thus form a ring, and $R^4$ and $R^5$ are more preferably linked together and thus form a hydrocarbon ring. The ring formed by $R^4$ and $R^5$ being linked together is preferably a 5-membered ring or a 6-membered ring.

In addition, from the viewpoint of synthesis, $R^2$, $R^3$, $R^6$, and $R^7$ are preferably hydrogen atoms.

In —$NR^6$— represented by Q or $Q^2$, preferred aspects of the alkyl group represented by $R^6$ are identical to the preferred aspects of that in a case in which $R^1$ or $R^8$ represents an alkyl group.

From the viewpoint of synthesis and the infrared-absorbing properties, each of $Q^1$ and $Q^2$ is independently —S— or a dialkylmethylene group, more preferably a dialkylmethylene group, and still more preferably a dimethyl methylene group.

In addition, $Q^1$ and $Q^2$ are preferably identical groups.

The aromatic ring or the heterocyclic aromatic ring that is formed of $T^1$ or $T^2$ may have a substituent. Examples of preferred aromatic rings or heterocyclic aromatic rings include benzene rings, naphthalene rings, pyridine rings, and pyrazine rings. Examples of preferred substituents include alkyl groups, alkoxy groups, dialkyl amino groups, chlorine atom, and sulfo groups.

Each of $T^1$ and $T^2$ may independently have a substituent, and the substituent is preferably a naphthalene ring or a benzene ring. In addition, the substituent is preferably an alkyl group having 1 to 8 carbon atoms and more preferably a methyl group.

In addition, $T^1$ and $T^2$ are preferably identical groups.

The counter anion represented by $A^-$ is a counter anion that neutralizes charges in all of the compounds represented by Formula (1). The counter anion may be a monovalent anion or a polyvalent anion such as a di- or higher-valent anion. In the case of a polyvalent anion, the compound represented by Formula (1) has structures other than $A^-$ as many as its valence. Among counter anions, examples thereof include halide ions, perchloric acid ions, tetraphenyl borate ions, tetrafluoroborate ions, hexafluorophosphate ions, and sulfonic acid ions, and tetrafluoroborate ions and hexafluorophosphate ions are preferred.

Preferred aspects of the alkyl group represented by $R^9$, $R^{10}$, $R^{11}$, or $R^{12}$ are identical to the preferred aspects of that in a case in which $R^1$ or $R^8$ represents an alkyl group. Among them, a methyl group or an ethyl group is particularly preferred.

The aryl group represented by $R^9$, $R^{10}$, $R^{11}$, or $R^{12}$ is preferably an aryl group having 6 to 30 carbon atoms, more preferably an aryl group having 6 to 20 carbon atoms, and most preferably an aryl group having 6 to 12 carbon atoms.

Specific examples thereof include phenyl groups, 1-naphthyl groups, 2-naphthyl groups, p-tolyl groups, p-chlorophenyl groups, p-fluorophenyl groups, p-methoxyphenyl groups, p-dimethylaminophenyl groups, p-methyl thiophenyl groups, p-phenylthiophenyl groups, and the like.

Among these aryl groups, phenyl groups, p-methoxyphenyl groups, and p-dimethylaminophenyl groups are preferred.

It is preferable that each of $R^{13}$ and $R^{14}$ is independently a hydrogen atom, an alkyl group, an aryl group, a halogen atom, $OR^{17}$, $NR^{18}R^{19}$, or $SR^{20}$, or $R^{13}$ and $R^{14}$ may be bonded together and thus form a ring, it is more preferable that each of $R^{13}$ and $R^{14}$ is independently a hydrogen atom, an alkyl group, a halogen atom, $OR^{17}$, $NR^{18}R^{19}$, or $SR^{20}$, or $R^{13}$ and $R^{14}$ form a ring bonded by an alkylene group, —O—, —$NR^{21}$—, —S—, or a group made of a combination of two or more thereof, and it is still more preferable that $R^{13}$ and $R^{14}$ form a ring bonded by an alkylene group, —O—, —$NR^{21}$—, —S—, or a group made of a combination of two or more thereof.

Each of $R^{15}$ and $R^{16}$ is preferably independently an alkyl group, an aryl group, a halogen atom, $OR^7$, $NR^{18}R^{19}$, or $SR^{20}$ and more preferably independently an alkyl group or a halogen atom.

Preferred aspects of the alkyl group represented by $R^{13}$, $R^{14}$, $R^{15}$, $R^{16}$, $R^{17}$, $R^{18}$, $R^{19}$, or $R^{20}$ are identical to the preferred aspects of that in a case in which $R^1$ or $R^8$ represents an alkyl group.

Preferred aspects of the aryl group represented by $R^{13}$, $R^{14}$, $R^{15}$, $R^{16}$, $R^{17}$, $R^{18}$, $R^{19}$, or $R^{20}$ are identical to the preferred aspects of that in a case in which $R^9$, $R^{10}$, $R^{11}$, or $R^{12}$ represents an aryl group.

In addition, from the viewpoint of color-developing properties, it is preferable that both $R^{13}$ and $R^{14}$ are hydrogen atoms or form a ring using an alkylene group, —O—, —$NR^{21}$—, —S—, or a group made of a combination of two or more thereof, it is more preferable that both $R^{13}$ and $R^{14}$ form a ring using an alkylene group, —O—, —$NR^{21}$—, —S—, or a group made of a combination of two or more thereof, it is still more preferable that both $R^{13}$ and $R^{14}$ form a ring using —O—, —$NR^{21}$—, or —S—, and it is particularly preferable that both $R^{13}$ and $R^{14}$ form a ring using —O— or —S—.

Examples of the halogen atom represented by $R^{15}$ or $R^{16}$ include chlorine atom, bromine atom, and iodine atom, and chlorine atom is preferred.

Each of n1 and n2 is preferably independently an integer of 0 to 2, more preferably 0 or 1, and particularly preferably 0.

From the viewpoint of color-developing properties, the number of carbon atoms in $X^1$ is preferably in a range of 1 to 60, more preferably in a range of 2 to 40, still more preferably in a range of 3 to 20, and particularly preferably in a range of 3 to 15. In addition, from the viewpoint of color-developing properties, the total number of carbon atoms in $X^1$ is preferably 60 or smaller, more preferably 40 or smaller, still more preferably 20 or smaller, and particularly preferably 15 or smaller. In addition, the total number thereof is preferably 3 or greater.

From the viewpoint of synthesis, $X^1$ is preferably a group that bonds to an alkenylene group side (a conjugated chain side) using an oxygen atom.

In addition, from the viewpoint of decomposition properties, $X^1$ is preferably a group that bonds to a carbonyl group side using a carbon atom or a nitrogen atom, more preferably a group that bonds to a carbonyl group side using a carbon atom, still more preferably a group that bonds to a carbonyl group side using a methylene group, and particularly preferably a group that bonds to a carbonyl group side using —$CH_2$—S—.

In addition, $X^1$ is preferably a group formed by bonding one or more of —O—, —S—, and/or a urethane bond to one or more of divalent hydrocarbon groups, more preferably a group formed by bonding one or more of —O—'s, one or more of —S— and/or urethane bonds, and two or more of divalent hydrocarbon groups or a group formed by bonding two or more of —O—'s and one or more of divalent hydrocarbon groups, still more preferably a group formed by bonding one or more of —O—'s, one or more of —S— and/or urethane bonds, and two or more of divalent hydrocarbon groups, and particularly preferably —$CH_2$—S— (arylene group) or —O—.

Examples of the divalent hydrocarbon group in $X^1$ include alkylene groups, arylene groups, and groups formed by a combination of two or more thereof. The alkylene group may have a branched or cyclic structure and is preferably an alkylene group having 1 to 20 carbon atoms and more preferably an alkylene group having 1 to 10 carbon atoms. The arylene group is preferably an arylene group having 6 to 20 carbon atoms, more preferably an arylene group having 6 to 12 carbon atoms, and still more preferably a phenylene group.

In addition, $X^1$ is preferably a group having at least —S—.

The compound represented by Formula (1) is preferably a compound represented by Formula (2) below.

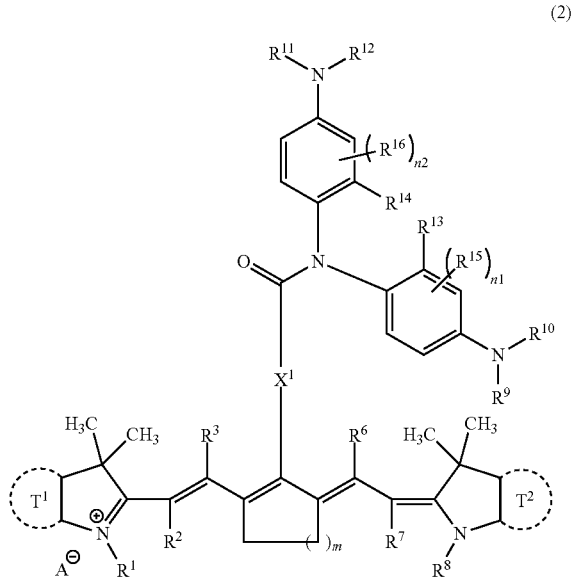

(2)

In Formula (2), each of $R^1$ and $R^8$ independently represents an alkyl group, each of $R^2$, $R^3$, $R^6$, and $R^7$ independently represents a hydrogen atom or an alkyl group, each of $T^1$ and $T^2$ independently represents an aromatic ring or a heterocyclic aromatic ring, $X^1$ represents a group formed by bonding one or more of —O—, —S—, and/or a urethane bond to one or more of divalent hydrocarbon groups, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom, an alkyl group, a halogen atom, $OR^{17}$, $NR^{18}R^{19}$, or $SR^{20}$, $R^{13}$ and $R^{14}$ may form a ring bonded by an alkylene group, —O—, —$NR^{21}$—, —S—, or a group made of a combination of two or more thereof, each of $R^{15}$ and $R^{16}$ independently represents an alkyl group, a halogen atom, $OR^{17}$, $NR^{18}R^{19}$, or $SR^{20}$, each of $R^{17}$, $R^{18}$, $R^{19}$, and $R^{20}$ independently represents an alkyl group or an aryl group, $R^{21}$ represents a hydrogen atom, an alkyl group, or an aryl group, each of n1 and n2 independently represents an integer of 0 to 3, and m represents 1 or 2.

$R^1$, $R^2$, $R^3$, $R^6$, $R^7$, $R^8$, $R^9$, $R^{10}$, $R^{11}$, $R^{12}$, n1, n2, $X^1$, $T^1$, $T^2$, and $A^-$ in Formula (2) are respectively identical to $R^1$, $R^2$, $R^3$, $R^6$, $R^7$, $R^8$, $R^9$, $R^{10}$, $R^{11}$, $R^{12}$, n1, n2, $X^1$, $T^1$, $T^2$, and $A^-$ in Formula (1), and preferred aspects thereof are also identical.

$R^{13}$ and $R^{14}$ in Formula (2) preferably form a ring bonded by an alkylene group, —O—, —$NR^{21}$—, —S—, or a group made of a combination of two or more thereof.

Each of $R^{15}$ and $R^{16}$ is preferably independently an alkyl group or a halogen atom.

In addition, $R^{17}$, $R^{18}$, $R^{19}$, $R^{20}$, and $R^{21}$ in $R^{13}$, $R^{14}$, $R^{15}$, and $R^{16}$ in Formula (2) are identical to $R^{17}$, $R^{18}$, $R^{19}$, $R^{20}$, and $R^{21}$ in $R^{13}$, $R^{14}$, $R^{15}$, and $R^{16}$ in Formula (1) described above, and preferred aspects thereof are also identical.

The compound represented by Formula (1) is preferably a compound represented by Formula (3) below.

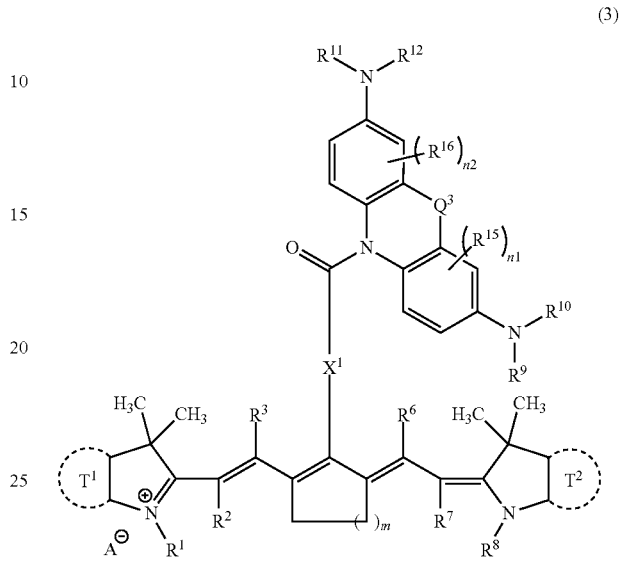

(3)

In Formula (3), each of $R^1$ and $R^8$ independently represents an alkyl group, each of $R^2$, $R^3$, $R^6$, and $R^7$ independently represents a hydrogen atom or an alkyl group, each of $T^1$ and $T^2$ independently represents an aromatic ring or a heterocyclic aromatic ring, $X^1$ represents a group formed by bonding one or more of —O—, —S—, and/or a urethane bond to one or more of divalent hydrocarbon groups, $A^-$ represents a counter anion, each of $R^9$, $R^{10}$, $R^{11}$, and $R^{12}$ independently represents an alkyl group or an aryl group, each of $R^{15}$ and $R^{16}$ independently represents a hydrogen atom, an alkyl group, a halogen atom, $OR^{17}$, $NR^{18}R^{19}$, or $SR^{20}$, each of $R^{17}$, $R^{18}$, $R^{19}$, and $R^{20}$ independently represents an alkyl group or an aryl group, each of n1 and n2 independently represents an integer of 0 to 3, m represents 1 or 2, $Q^3$ represents —O—, —$NR^{22}$—, or —S—, and $R^{22}$ represents an alkyl group or an aryl group.

$R^1$, $R^2$, $R^3$, $R^6$, $R^7$, $R^8$, $R^9$, $R^{10}$, $R^{11}$, $R^{12}$, n1, n2, $X^1$, $T^1$, $T^2$, and $A^-$ in Formula (3) are respectively identical to $R^1$, $R^2$, $R^3$, $R^6$, $R^7$, $R^8$, $R^9$, $R^{10}$, $R^{11}$, $R^{12}$, n1, n2, $X^1$, $T^1$, $T^2$, and $A^-$ in Formula (1), and preferred aspects thereof are also identical. $R^{15}$, $R^{16}$, and m in Formula (3) are respectively identical to $R^{15}$, $R^{16}$, and m in Formula (2), and preferred aspects thereof are also identical.

In addition, $R^{17}$, $R^{18}$, $R^{19}$, $R^{20}$, and $R^{21}$ in $R^{13}$, $R^{14}$, $R^{15}$, and $R^{16}$ in Formula (3) are identical to $R^{17}$, $R^{18}$, $R^{19}$, $R^{20}$, and $R^{21}$ in $R^{13}$, $R^{14}$, $R^{15}$, and $R^{16}$ in Formula (1) described above, and preferred aspects thereof are also identical.

$Q^3$ is preferably —O—, or —S— and more preferably —O—.

Preferred aspects of the alkyl group or the aryl group represented by $R^{22}$ are identical to the preferred aspects of that in a case in which $R^9$, $R^{10}$, $R^{11}$, or $R^{12}$ represents an alkyl group or an aryl group.

Hereinafter, preferred specific examples W-1 to W-14 of the compound represented by Formula (1) will be illustrated, but the present invention is not limited thereto.

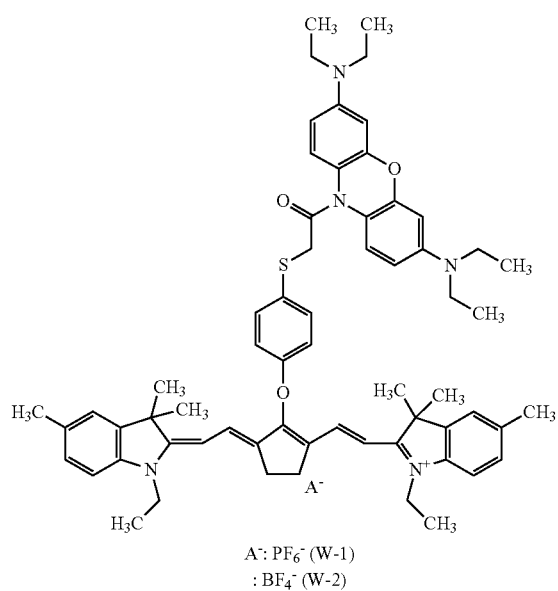
A⁻: PF₆⁻ (W-1)
: BF₄⁻ (W-2)
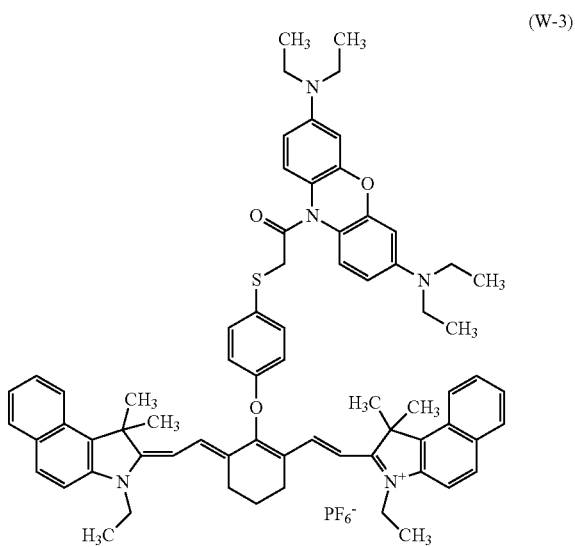
(W-3)
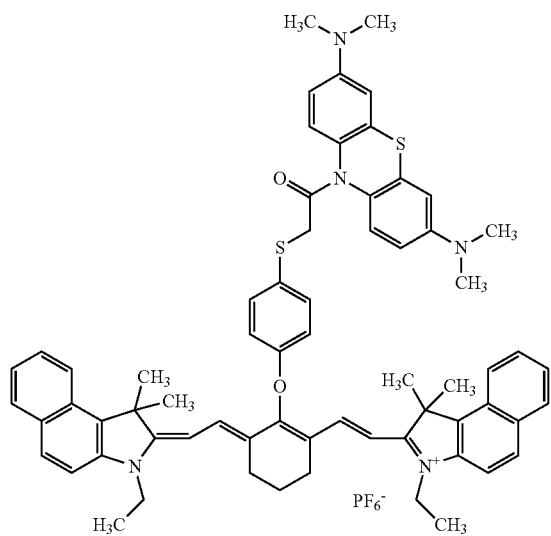
(W-4)
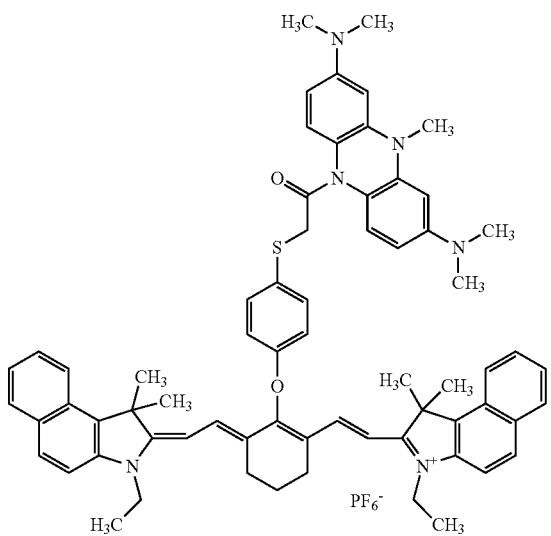
(W-5)

-continued
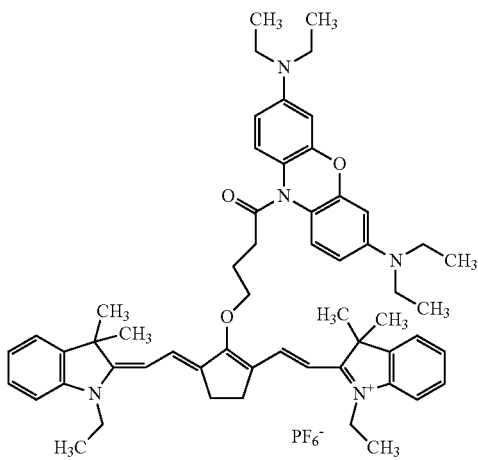
(W-6)
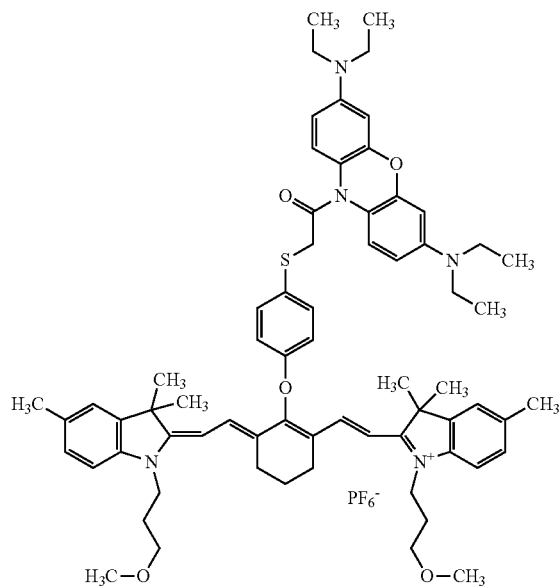
(W-7)
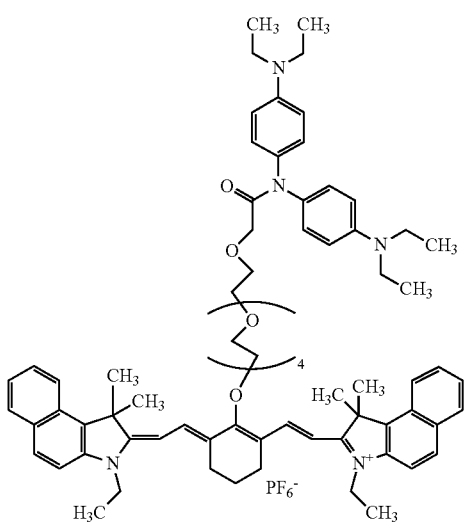
(W-8)
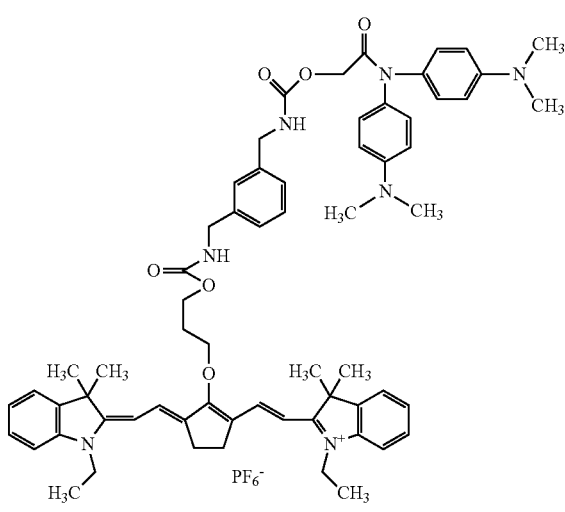
(W-9)

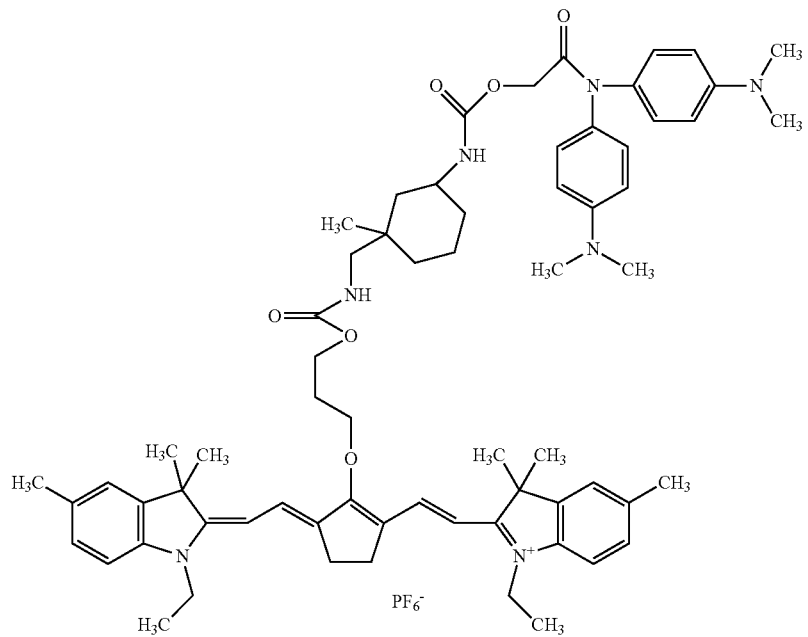
(W-10)
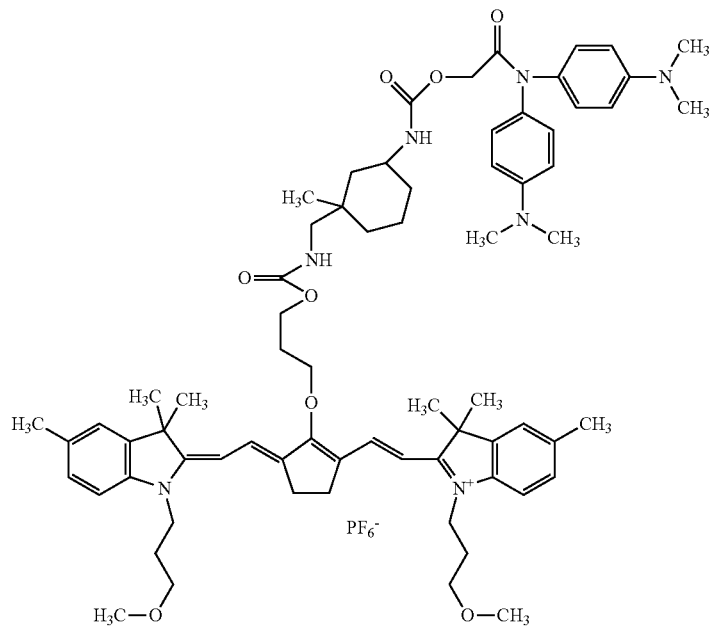
(w-11)

-continued

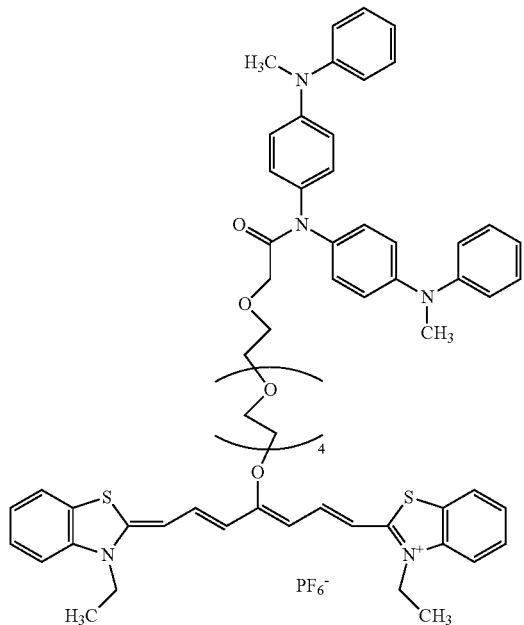
(W-12)

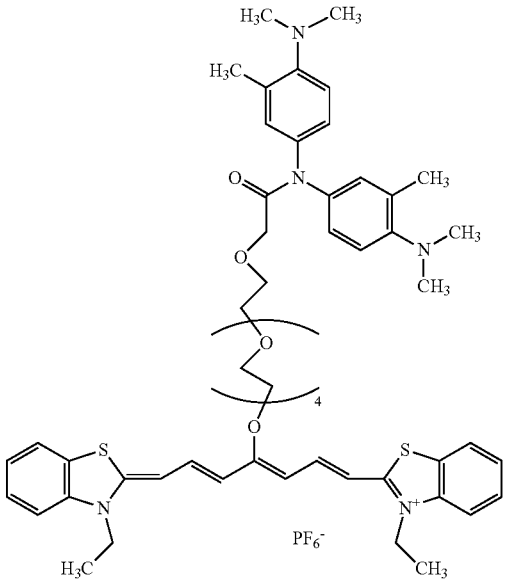
(W-13)

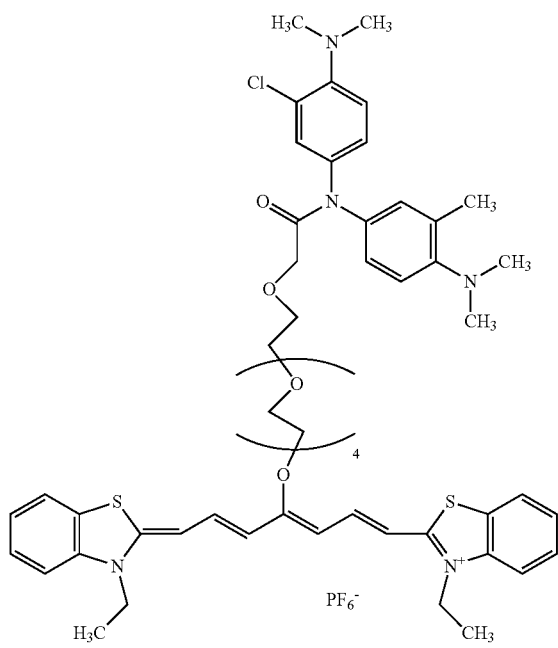
(W-14)

To the infrared-sensitive color developing composition of the present invention or an image-recording layer in a lithographic printing plate precursor described below, it is possible to add an arbitrary amount of the compound represented by Formula (1), but the content of the compound is preferably in a range of 0.1% by mass to 50% by mass, more preferably in a range of 0.5% by mass to 30% by mass, and still more preferably in a range of 1% by mass to 20% by mass of the total solid content of the infrared-sensitive color developing composition or the image-recording layer in the lithographic printing plate precursor. Meanwhile, the total solid content refers to the total amount of components in the composition or the layer excluding volatile components such as a solvent.

The synthesis method for the compound represented by Formula (1) is not particularly limited, and preferred examples thereof include an ordinary synthesis method illustrated below as a synthesis scheme.

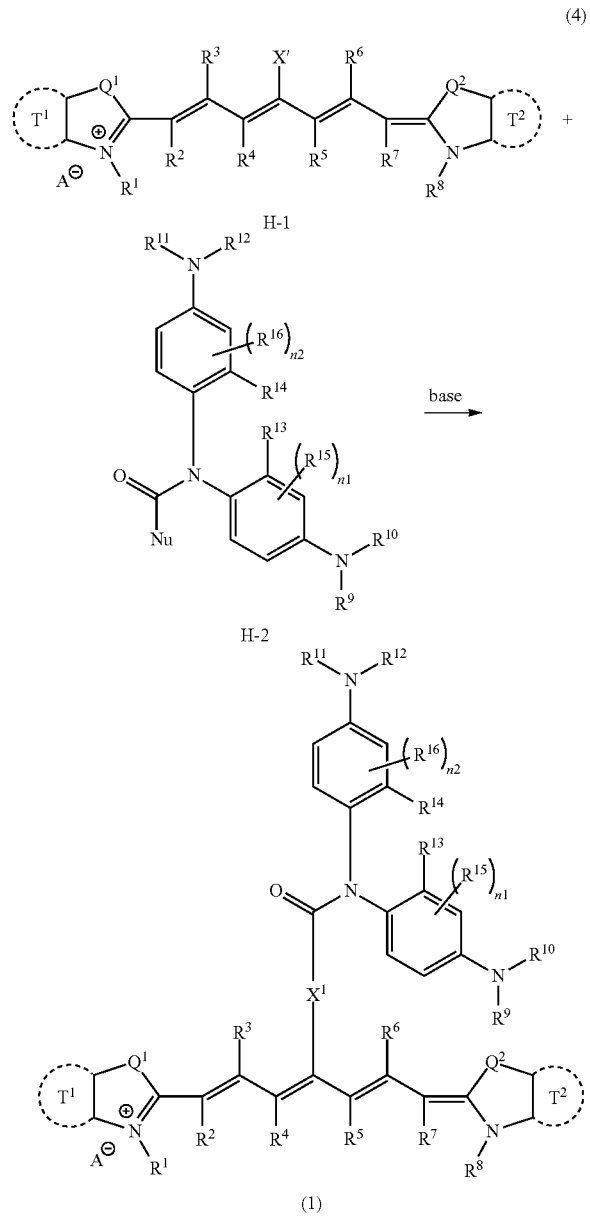

As illustrated in Formula (4), the compound can be obtained by, for example, making a skeleton H-2 having a nucleophilic group Nu act on an infrared-absorbing skeleton H-1 in which a leaving group X' is substituted in the presence of a base. Meanwhile, Nu represents a group which turns into a linking group $X^1$ after the reaction. Preferred examples of X' include halogen atoms. In addition, preferred examples of Nu include groups having a hydroxy group or a mercapto group in the terminal.

(Component B) Binder Polymer

The infrared-sensitive color developing composition of the present invention preferably includes a binder polymer (Component B).

The binder polymer that can be used in the present invention is not particularly limited, and well-known binder polymers that are used for photosensitive color developing compositions can be used. In addition, the binder polymer is preferably one of polymers having membrane properties. Among these, acrylic resins, polyvinyl acetal resins, and polyurethane resins are preferred.

Preferred examples of the binder polymer that can be used in the infrared-sensitive color developing composition of the present invention include polymers having a crosslinking functional group for improving the membrane strengths of image portions in main chains or side chains, preferably, in side chains as described in JP2008-195018A. Crosslinking is formed between polymer molecules through crosslinking functional groups, and curing is accelerated.

The crosslinking functional groups are preferably ethylenic unsaturated groups such as (meth)acrylic groups, vinyl group, and allyl groups, epoxy groups, or the like, and these groups can be introduced into polymers through polymer reactions or copolymerization. For example, it is possible to use reactions between acryl polymers or polyurethane having carboxy groups in side chains and glycidyl methacrylate or reactions between polymers having epoxy resins and ethylenic unsaturated group-containing carboxylic acids such as methacrylic acid.

The content of the crosslinking functional groups in the binder polymer is preferably in a range of 0.1 mmol to 10.0 mmol, more preferably in a range of 1.0 mmol to 7.0 mmol, and particularly preferably in a range of 2.0 mmol to 5.5 mmol per gram of the binder polymer.

As the binder polymer that can be used in the infrared-sensitive color developing composition of the present invention, it is also possible to use polymers having acid groups. Examples of the polymers having acid groups include polymers containing carboxylic acid groups (including salts thereof). As the above-described polymers, addition polymers having carboxylic acid groups in side chains, for example, polymers described in each of JP1984-44615B (JP-S59-44615B), JP1979-34327B (JP-S54-34327B), JP1983-12577B (JP-S58-12577B), JP1979-25957B (JP-S54-25957B), JP1979-92723A (JP-S54-92723A), JP1984-53836A (JP-S59-53836A), and JP1984-71048A (JP-S59-71048A), that is, methacrylic acid copolymers, acrylic acid copolymers, itaconic acid copolymers, crotonic acid copolymers, maleic acid copolymers, partially esterified maleic acid copolymers, and the like are useful. The binder is preferably a copolymer containing a monomer unit derived from (meth)acrylic acid esters having carboxylic acid groups.

A preferred example of polymers having carboxylic acid groups is a copolymer having (a) monomer units containing carboxylic acid groups and (b) monomer units imparting radical crosslinking properties.

The monomer units containing carboxylic acid groups (a) are not particularly limited, and structures described in JP2002-40652A and Paragraphs "0059" to "0075" of JP2005-300650A are preferably used.

The monomer units imparting radical crosslinking properties (b) are not particularly limited, and structures described in Paragraphs "0041" to "0053" of JP2007-248863A are preferably used.

The polymers having carboxylic acid groups may have monomer units derived from ethylenic unsaturated compounds including neither carboxylic acid groups nor radical crosslinking groups as copolymerization components. As the above-described monomer units, monomer units derived from (meth)acrylic acid esters or (meth)acrylic acid amides are preferred. Particularly, monomer units derived from (meth)acrylic acid amides described in Paragraphs "0061" to "0084" of JP2007-272134A are preferably used. The content of the above-described monomer units is preferably in a range of 5 units to 50 units, more preferably in a range of 5 units to 35 units, and still more preferably in a range of 5 units to 25 units in a case in which the total number of monomer units is set to 100.

As the binder polymer, it is also possible to use a urethane resin having crosslinking groups in side chains in addition to the addition polymers consisting of a combination of the above-described monomer units. Here, the crosslinking group refers to a group capable of crosslinking binder polymers through chemical reactions occurring in color developing compositions when being exposed. Regarding the crosslinking groups, there are no particular limitations on the chemical structures thereof as long as the groups have the above-described function; however, for example, ethylenic unsaturated groups are preferred as functional groups that are capable of addition polymerization. In addition, examples thereof include functional groups described in Paragraphs "0130" to "0139" of JP2007-17948A.

To the infrared-sensitive color developing composition or the image-recording layer in the lithographic printing plate precursor, it is possible to add an arbitrary amount of the binder polymer, but the content of the binder polymer is preferably in a range of 10% by mass to 95% by mass and more preferably in a range of 20% by mass to 90% by mass of the total solid content of the infrared-sensitive color developing composition or the image-recording layer in the lithographic printing plate precursor.

The binder polymer that is used in the image-recording layer in the lithographic printing plate precursor of the present invention described below is preferably a binder polymer that is used in on-machine development-type lithographic printing plate precursors (hereinafter, also referred to as the binder polymer for on-machine development).

The binder polymer for on-machine development is preferably a binder polymer having alkylene oxide chains. The binder polymer having alkylene oxide chains may have poly(alkylene oxide) portions in main chains or side chains and may be graft polymers having poly(alkylene oxide) in side chains or block copolymers of blocks constituted of repeating units containing poly(alkylene oxide) and blocks constituted of repeating units not containing (alkylene oxide).

In a case in which the binder polymer has poly(alkylene oxide) portions in main chains, polyurethane resins are preferred. Examples of polymers in main chains in a case in which the binder polymer has poly(alkylene oxide) portions in side chains include (meth)acrylic resins, polyvinyl acetal resins, polyurethane resins, polyurea resins, polyimide resins, polyamide resins, epoxy resins, polystyrene resins, novolac-type phenol resins, polyester resins, synthetic rubber, and natural rubber, and (meth)acrylic resins are particularly preferred.

The alkylene oxide is preferably an alkylene oxide having 2 to 6 carbon atoms and particularly preferably an ethylene oxide or a propylene oxide.

The repeating number of the alkylene oxide in the poly(alkylene oxide) portion is preferably in a range of 2 to 120, more preferably in a range of 2 to 70, and still more preferably in a range of 2 to 50.

When the repeating unit of the alkylene oxide is 120 or smaller, there are no cases in which printing resistance is degraded due to both friction and ink-receiving properties, which is preferable.

The poly(alkylene oxide) portion is preferably included in a structure represented by Formula (AO) below as the side chain of the binder and more preferably included in the structure represented by Formula (AO) below as the side chain of the (meth)acrylic resin.

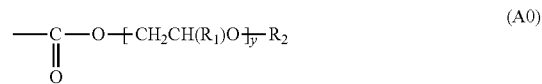

In Formula (AO), y represents 2 to 120, $R_1$ represents a hydrogen atom or an alkyl group, and $R_2$ represents a hydrogen atom or a monovalent organic group.

The monovalent organic group is preferably an alkyl group having 1 to 6 carbon atoms, and examples thereof include a methyl group, an ethyl group, an n-propyl group, an isopropyl group, an n-butyl group, a sec-butyl group, an isobutyl group, a tert-butyl group, an n-pentyl group, an isopentyl group, a neopentyl group, an n-hexyl group, an isohexyl group, 1,1-dimethyl butyl group, 2,2-dimethyl butyl group, a cyclopentyl group, and cylcohexyl group.

In Formula (AO), y is preferably 2 to 70 and more preferably 2 to 50. $R_1$ is preferably a hydrogen atom or a methyl group and particularly preferably a hydrogen atom. $R_2$ is particularly preferably a hydrogen atom or a methyl group.

In order to improve the membrane strengths of image portions, the binder polymer may have crosslinking properties. In order to impart crosslinking properties to the polymer, it is necessary to introduce crosslinking functional groups such as ethylenic unsaturated bonds into main chains or side chains of the polymer. The crosslinking functional group may be introduced by means of copolymerization.

Examples of polymers having ethylenic unsaturated bonds in main chains of the polymers include poly-1,4-butadiene, poly-1,4-isoprene, and the like.

Examples of polymers having ethylenic unsaturated bonds in side chains of the polymers include polymers of esters or amides of acrylic acid or methacrylic acid in which residues (R of —COOR or —CONHR) of the esters or the amides have ethylenic unsaturated bonds.

Examples of residues (the above-described R) having ethylenic saturated bonds include —(CH$_2$)$_n$CR$^{1A}$=CR$^{2A}$R$^{3A}$, —(CH$_2$O)$_n$CH$_2$CR$^{1A}$CR$^{2A}$R$^{3A}$, —(CH$_2$CH$_2$O)$_n$CH$_2$CR$^{1A}$=CR$^{2A}$R$^{3A}$, —(CH$_2$)$_n$NH—CO—O—CH$_2$CR$^{1A}$—R$^{2A}$R$^{3A}$, —(CH$_2$)$_n$—O—CO—CR$^{1A}$CR$^{2A}$R$^{3A}$, and —(CH$_2$CH$_2$O)$_2$—X (in the formulae, each of R$^{A1}$ to R$^{A3}$ independently represents a hydrogen atom, a halogen atom, an alkyl group having 1 to 20 carbon atoms, an aryl group, an alkoxy group, or an arylory group, and R$^{A1}$ and R$^{A2}$ or R$^{A3}$ may be bonded together and thus form a ring. n represents an integer of 1 to 10. X represents a dicyclopentadienyl residue.).

Specific examples of ester residues include —CH$_2$CH=CH$_2$ (described in JP1995-21633B (JP-H07-21633B)), —CH$_2$CH$_2$O—CH$_2$CH=CH$_2$, —CH$_2$C(CH$_3$)=CH$_2$, —CH$_2$CH=CH—C$_6$H$_5$, —CH$_2$CH$_2$OCOCH=CH—C$_6$H$_5$, —CH$_2$CH$_2$—NHCOO—CH$_2$CH=CH$_2$, and —CH$_2$CH$_2$O—X (in the formula, X represents a dicyclopentadienyl residue.).

Specific examples of amide residues include —CH$_2$CH=CH$_2$, —CH$_2$CH$_2$—Y (in the formula, Y represents a cyclohexene residue.), —CH$_2$CH$_2$—OCO=CH$_2$.

In the binder having crosslinking properties, for example, free radicals (living radicals in polymerization processes of polymerization-initiating radicals or polymerizable compounds) are added to the crosslinking functional groups, the free radicals are addition-polymerized between polymers directly or through polymerization closed chains of the polymerizable compounds, and crosslinking is formed between polymer molecules, thereby curing the composition. Alternatively, atoms in polymers (for example, hydrogen atoms on carbon atoms adjacent to the crosslinking functional groups) are drawn off by free radicals, thus, polymer radicals are generated, and the polymer radicals are bonded to each other, whereby crosslinking is formed between polymer molecules, and the composition is cured.

The content of the crosslinking groups in the binder polymer (the content of unsaturated double bonds that can be radical-polymerized by means of iodimetry) is preferably in a range of 0.1 mmol to 10.0 mmol, more preferably in a range of 1.0 mmol to 7.0 mmol, and particularly preferably in a range of 2.0 mmol to 5.5 mmol per gram of the binder polymer from the viewpoint of a favorable sensitivity and favorable storage stability.

Hereinafter, specific examples (1) to (11) of the binder polymer for on-machine development will be illustrated, but the present invention is not limited thereto. In the following exemplary compounds, numeric values shown beside individual repeating units (numeric values shown beside main chain repeating units) represent the molar percentages of the repeating units. The numeric values shown beside the repeating units of side chains represent the repeating numbers of the repeating units. In addition, Me represents a methyl group.

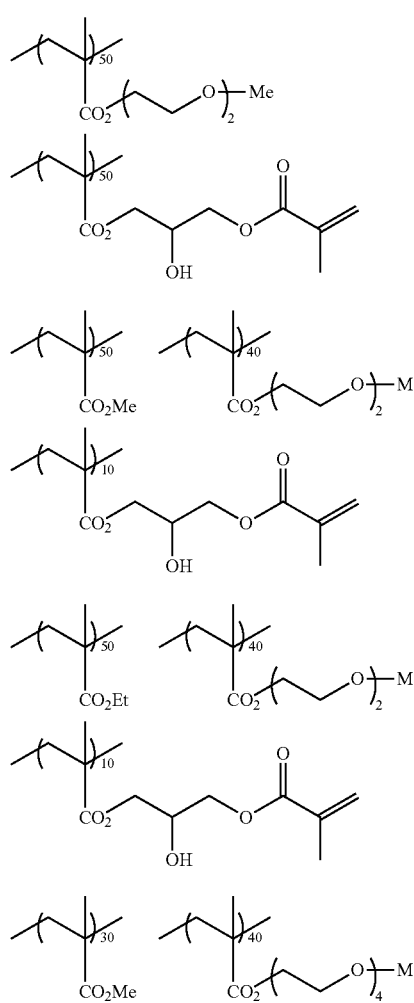

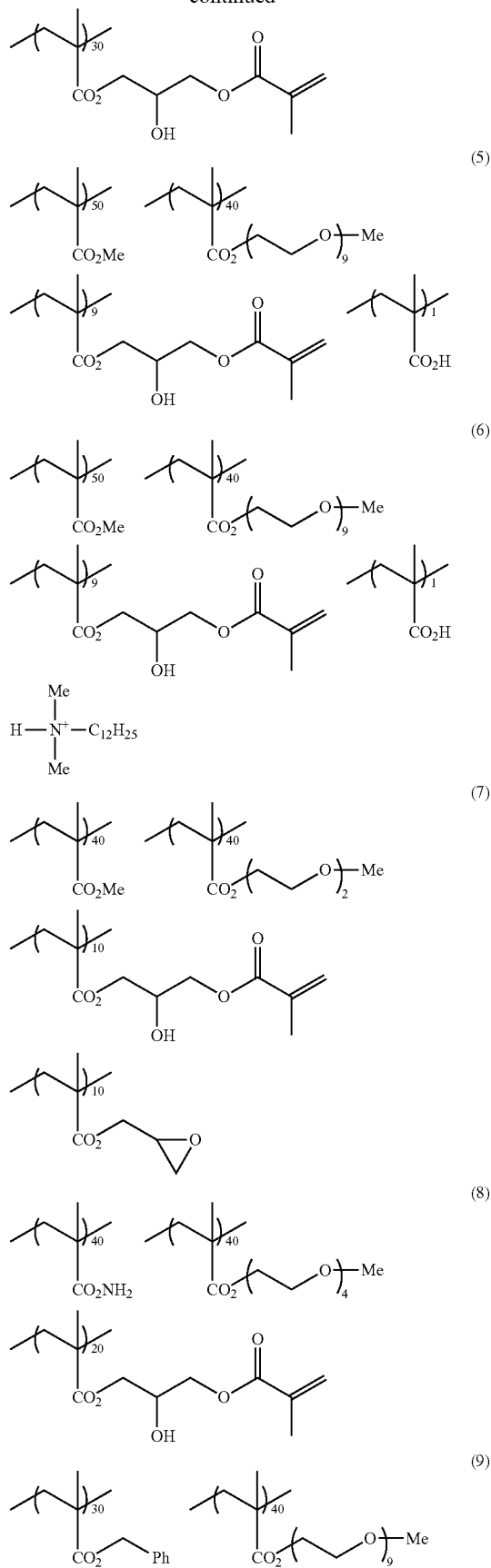

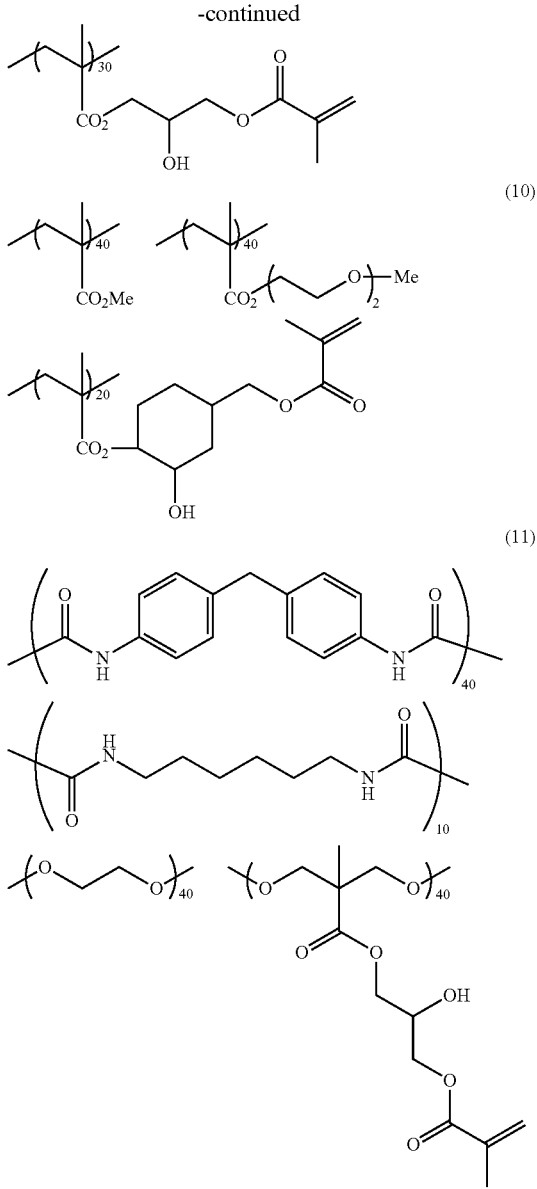

Regarding the molecular weight of the binder polymer, the mass-average molar mass (weight-average molecular weight, Mw) as a polystyrene equivalent value obtained by a GPC method is preferably 2,000 or greater, more preferably 5,000 or greater, and still more preferably in a range of 10,000 to 300,000.

In the present invention, it is possible to jointly use hydrophilic polymers such as polyacrylic acid and polyvinyl alcohols described in JP2008-195018A as necessary. In addition, it is also possible to jointly use lipophilic polymers and hydrophilic polymers.

In a case in which the infrared-sensitive color developing composition of the present invention is applied to image-recording layers in lithographic printing plate precursors, the form of the binder polymer may be present as a binder that plays a role of joining individual components or may be present in a particulate form in the infrared-sensitive color developing composition. In a case in which the binder polymer is present in a particulate form, the average primary particle diameter is preferably in a range of 10 nm to 1,000 nm, more preferably in a range of 20 nm to 300 nm, and particularly preferably in a range of 30 nm to 120 nm.

(Component C) Polymerization Initiator

The infrared-sensitive color developing composition of the present invention preferably includes a polymerization initiator (Component C). The present inventors and the like found that the polymerization initiator in the infrared-sensitive color developing composition of the present invention does not polymerize a polymerizable compound (Component D) described below but also, even in a case in which the polymerizable compound is not included, while a detailed mechanism thereof is unclear, further enhances the color-developing properties of the composition after infrared exposure. The above-described effect is more significant in a case in which an onium salt is used as the polymerization initiator.

While a detailed mechanism of color-developing properties being excellent when an onium salt is included is unclear, the present inventors and the like assume that, since the onium salt has a low energy level in the lowest unoccupied molecular orbital (LUMO), structures having conjugated chains in which $R^1$ to $R^8$ and the like bonded together are one-electron-oxidized through the onium salt, and the electron-accepting function is further enhanced, whereby electron migration from structures having N,N-bis(p-aminoaryl)amide structures to the structures having conjugated chains in which $R^1$ to $R^8$ and the like bonded together is accelerated, and color-developing properties become superior.

The polymerization initiator that is used in the infrared-sensitive color developing composition of the present invention is a compound that generates polymerization-initiating seeds such as radicals or cations using the energies of either or both light and heat, and it is possible to appropriately select and use well-known thermopolymerization initiators, compounds having bonds with a small bond dissociation energy, photopolymerization initiators, and the like.

The polymerization initiator is preferably a radical polymerization initiator and more preferably an onium salt.

In addition, the polymerization initiator is preferably an infrared-sensitive polymerization initiator.

The polymerization initiator may be used singly, or two or more polymerization initiators may be jointly used.

Examples of the radical polymerization initiator include (a) organic halides, (b) carbonyl compounds, (c) azo compounds, (d) organic peroxides, (e) metallocene compounds, (f) azide compounds, (g) hexaarylbiimidazole compounds, (h) organic borate compounds, (i) disulfone compounds, (j) oxime ester compounds, and (k) onium salt compounds.

(a) The organic halides are preferably, for example, compounds described in Paragraphs "0022" and "0023" of JP2008-195018A.

(b) The carbonyl compounds are preferably, for example, compounds described in Paragraph "0024" of JP2008-195018A.

(c) As the azo compounds, it is possible to use, for example, azo compounds described in JP 1996-108621A (JP-H08-108621A).

(d) The organic peroxides are preferably, for example, compounds described in Paragraph "0025" of JP2008-195018A.

(e) The metallocene compounds are preferably, for example, compounds described in Paragraph "0026" of JP2008-195018A.

(f) Examples of the azide compounds include compounds such as 2,6-bis(4-azidebenzylidene)-4-methylcyclohexanone.

(g) The hexaarylbiimidazole compounds are preferably, for example, compounds described in Paragraph "0027" of JP2008-195018A.

(h) The organic borate compounds are preferably, for example, compounds described in Paragraph "0028" of JP2008-195018A.

(i) Examples of the disulfone compounds include compounds described in each of JP 1986-166544A (JP-S61-166544A) and JP2002-328465A.

(j) The oxime ester compounds are preferably, for example, compounds described in Paragraphs "0028" to "0030" of JP2008-195018A.

Among the above-described polymerization initiators, from the viewpoint of curing properties, more preferred examples of the polymerization initiator include oxime esters and onium salts, and still more preferred examples thereof include onium salts such as iodonium salts, sulfonium salts, and azinium salts. In addition, in a case in which the polymerization initiator is used in lithographic printing plate precursors, iodonium salts and sulfonium salts are particularly preferred. Specific examples of these compounds will be described below, but the present invention is not limited thereto.

Examples of the iodonium salts are preferably diphenyl iodonium salts, particularly preferably diphenyl iodonium salts substituted with electron-donating groups, for example, alkyl groups or alkoxyl groups, and preferably asymmetric diphenyl iodonium salts. Specific examples thereof include diphenyliodonium=hexafluorophosphate, 4-methoxyphenyl-4-(2-methylpropyl) phenyliodonium=hexafluorophosphate, 4-(2-methylpropyl)phenyl-p-tolyliodonium=hexafluorophosphate, 4-hexyloxyphenyl-2,4,6-trimethoxyphenyl iodonium=hexafluorophosphate, 4-hexyloxyphenyl-2,4-diethoxyphenyl iodonium=tetrafluoroborate, 4-octyloxyphenyl-2,4,6-trimethoxyphenyl iodonium=1-perfluorobutane sulfonate, 4-octyloxyphenyl-2,4,6-trimethoxyphenyliodonium=hexafluorophosphate, and bis(4-t-butylphenyl)iodonium=hexafluorophosphate.

Examples of the sulfonium salts are preferably triarylsulfonium salts, particularly preferably triarylsulfonium salts in which at least some of electron-attracting groups, for example, groups on aromatic rings are substituted with halogen atoms, and still more preferably triarylsulfonium salts in which the total number of substituted halogen atoms on aromatic rings is four or greater. Specific examples thereof include triphenylsulfonium=hexafluorophosphate, triphenylsulfonium=benzoyl formate, bis(4-chlorophenyl)phenyl sulfonium=benzoyl formate, bis(4-chlorophenyl)-4-methylphenylsulfonium=tetrafluoroborate, tris(4-chlorophenyl)sulfonium=3,5-bis(methoxycarbonyl) benzenesulfonate, tris(4-chlorophenyl)sulfonium=hexafluorophosphate, and tris(2,4-dichlorophenyl)sulfonium=hexafluorophosphate.

The content of the polymerization initiator is preferably in a range of 0.1% by mass to 50% by mass, more preferably in a range of 0.5% by mass to 30% by mass, and particularly preferably in a range of 0.8% by mass to 20% by mass of the total solid content of the infrared-sensitive color developing composition or the image-recording layer in the lithographic printing plate precursor.

(Component D) Polymerizable Compound

The infrared-sensitive color developing composition of the present invention preferably includes a polymerizable compound (Component D). The infrared-sensitive color developing composition of the present invention including the polymerizable compound is a color developing curable composition having a polymerization curing function in addition to color-developing properties by means of infrared exposure.

In addition, the infrared-sensitive color developing composition of the present invention can be preferably used as a curable composition including the polymerization initiator (Component C) and the polymerizable compound (Component D) and can be more preferably used as an infrared ray-curable or infrared-sensitive color developing composition.

The polymerizable compound (Component D) that is used in the infrared-sensitive color developing composition of the present invention may be, for example, a radical polymerizable compound or a cationic polymerizable compound, but is preferably an addition polymerizable compound having at least one ethylenic unsaturated bond (ethylenic unsaturated compound). The ethylenic unsaturated compound is preferably a compound having at least one terminal ethylenic unsaturated bond and more preferably a compound having two or more terminal ethylenic unsaturated bonds. The polymerizable compound has a chemical form, for example, a monomer, a prepolymer, that is, a dimer, a trimer, or an oligomer, or a mixture thereof.

Examples of the monomer include unsaturated carboxylic acids (for example, acrylic acid, methacrylic acid, itaconic acid, crotonic acid, isocrotonic acid, maleic acid, and the like), esters thereof, and amides thereof, and esters of unsaturated carboxylic acids and polyhydric amine compounds and amides of unsaturated carboxylic acids and polyhydric alcohol compounds are preferably used. In addition, addition reaction products between unsaturated carboxylic acid esters or amides having nucleophilic substituents such as hydroxy groups, amino groups, or mercapto groups and monofunctional or polyfunctional isocyanates or epoxies, dehydration condensation reaction products with monofunctional or polyfunctional carboxylic acids, and the like are also preferably used. In addition, addition reaction products between unsaturated carboxylic acid esters or amides having electrophilic substituents such as isocyanate groups and epoxy groups and monofunctional or polyfunctional alcohols, amines, or thiols, furthermore, substitution reaction products between unsaturated carboxylic acid esters or amides having dissociable substituents such as halogen atoms and tosyloxy groups and monofunctional or polyfunctional alcohols, amines, or thiols are also preferred. In addition, as additional examples, compound groups obtained by substituting the unsaturated carboxylic acids with unsaturated phosphonic acids, styrene, vinyl ethers, or the like can also be used. These monomers are described in JP2006-508380A, JP2002-287344A, JP2008-256850A, JP2001-342222A, JP 1997-179296A (JP-H09-179296A), JP 1997-179297A (JP-H09-179297A), JP1997-179298A (JP-H09-179298A), JP2004-294935A, JP2006-243493A, JP2002-275129A, JP2003-64130A, JP2003-280187A, JP1998-333321A (JP-H10-333321A), and the like.

As specific examples of monomers of esters of polyhydric alcohol compounds and unsaturated carboxylic acids, examples of acrylic acid esters include ethylene glycol diacrylate, 1,3-butanediol diacrylate, tetramethylene glycol diacrylate, propylene glycol diacrylate, trimethylolpropane triacrylate, hexanediol diacrylate, tetraethylene glycol diacrylate, pentaerythritol tetraacrylate, sorbitol triacrylate, isocyanuric acid ethylene oxide (EO)-modified triacrylate, polyester acrylate oligomers, and the like. Examples of methacrylic acid esters include tetramethylene glycol dimethacrylate, neopentyl glycol dimethacrylate, trimethylolpropane trimethacrylate, ethylene glycol dimethacrylate, pentaerythritol trimethacrylate, bis[p-(3-methacryloxy-2-hydroxypropoxy)phenyl] dimethyl methane, bis-[p-(methacryloxyethoxy)phenyl] dimethyl methane, and the like. In addition, specific examples of monomers of amides of polyhydric amine compounds and unsaturated carboxylic acids include methylenebis-acrylamide, methylenebis-methacrylamide, 1,6-hexamethylenebis-acrylamide, 1,6-hexamethylenebis-methacrylamide, diethylenetriamine trisacrylamide, xylylene bisacrylamide, xylylene bismethacrylamide, and the like.

In addition, urethane-based addition polymerizable compounds manufactured using addition reactions between isocyanates and hydroxy groups are also preferred, and specific examples thereof include vinyl urethane compounds containing two or more polymerizable vinyl groups in one monomer obtained by adding vinyl monomers containing hydroxy groups represented by General Formula (M) below to polyisocyanate compounds having two or more isocyanate groups in one molecule which is described in, for example, JP1973-41708B (JP-S48-41708B).

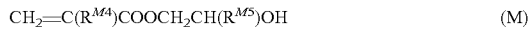

$$CH_2=C(R^{M4})COOCH_2CH(R^{M5})OH \quad (M)$$

In Formula (M), each of $R^{M4}$ and $R^{M5}$ independently represents a hydrogen atom or a methyl group.

In addition, urethane acrylates described in JP1976-37193A (JP-S51-37193A), JP1990-32293B (JP-H02-32293B), JP1990-16765B (JP-H02-16765B), JP2003-344997A, and JP2006-65210A, urethane compounds having ethylene oxide-based skeletons described in JP1983-49860B (JP-S58-49860B), JP1981-17654B (JP-S56-17654B), JP1987-39417B (JP-S62-39417B), JP1987-39418B (JP-S62-39418B), JP2000-250211A, and JP2007-94138A, and urethane compounds having hydrophilic groups described in U.S. Pat. No. 7,153,632B, JP1996-505958A (JP-H08-505958A), JP2007-293221A, and JP2007-293223A are also preferred.

The details of the structures of the polymerizable compound and the method for using the polymerizable compound such as whether the polymerizable compound is used singly or jointly and the amount of the polymerizable compound added can be arbitrarily set in consideration of the applications and the like of the final infrared-sensitive color developing composition or lithographic printing plate precursor.

The content of the polymerizable compound is preferably in a range of 5% by mass to 75% by mass, more preferably in a range of 10% by mass to 70% by mass, and particularly preferably in a range of 15% by mass to 60% by mass of the total solid content of the infrared-sensitive color developing composition or the image-recording layer in the lithographic printing plate precursor.

The infrared-sensitive color developing composition of the present invention may further include well-known additives that are generally used in the infrared-sensitive color developing composition or the image-recording layer in the lithographic printing plate precursor depending on the purposes.

The respective components of the infrared-sensitive color developing composition are dissolved or dispersed in an appropriate solvent so as to prepare a coating fluid, the coating fluid is applied and dried on an appropriate support or the like, color developing composition films are formed, and image-recording materials are preferably produced. Preferred example of the image-recording materials include image-recording materials in which color development by means of image exposure is used such as lithographic printing plate precursors, print wiring boards, color filters, and photomasks and image-recording materials in which color development and polymerization curing are used.

The image-recording materials produced using the infrared-sensitive color developing composition of the present invention develop colors when being exposed to light sources radiating infrared rays. Preferred examples of light sources include solid lasers, semiconductor lasers, and the like which radiate infrared rays.

In addition, the infrared-sensitive color developing composition of the present invention may include a sensitizing dye other than Component A, but preferably includes no sensitizing dye or a smaller content of a sensitizing dye than Component A, and more preferably includes no sensitizing dye.

As other sensitizing dyes, well-known sensitizing dyes can be used, and, for example, commercially available dyes and well-known dyes described in documents such as "Dye Handbook" (edited by The Society of Synthetic Organic Chemistry, Japan, published on 1970). Specific examples thereof include dyes such as azo dyes, metal complex salt azo dyes, pyrazolone azo dyes, naphthoquinone dyes, anthraquinone dyes, phthalocyanine dyes, carbonium dyes, quinone imine dyes, methine dyes, cyanine dyes, squarylium dyes, pyrylium salts, and metal thiolate complexes.

In the present invention, the infrared-sensitive color developing composition and compositions that form image-recording layers may be used for coating by dissolving or dispersing the respective components in a variety of solvents.

As the solvents, well-known solvents can be used. Specific examples thereof include acetone, methyl ethyl ketone (2-butanone), cyclohexane, ethyl acetate, ethylene dichloride, tetrahydrofuran, toluene, ethylene glycol monomethyl ether, ethylene glycol monoethyl ether, ethylene glycol dimethyl ether, propylene glycol monomethyl ether, propylene glycol monoethyl ether, acetylacetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 1-methoxy-2-propanol, 3-methoxy-1-propanol, methoxy methoxy ethanol, diethylene glycol monomethyl ether, diethylene glycol monoethyl ether, diethylene glycol dimethyl ether, diethylene glycol diethyl ether, propylene glycol monomethyl ether acetate, propylene glycol monoethyl ether acetate, 3-methoxypropyl acetate, N,N-dimethyl formamide, dimethyl sulfoxide, γ-butyrolactone, methyl lactate, ethyl lactate, and the like. These solvent may be used singly or two or more solvents may be used in a mixed form. Meanwhile, the concentration of solid contents in the coating fluid is preferably in a range of 1% by mass to 50% by mass. Meanwhile, the concentration of solid contents refers to the concentration of all components excluding solvents.

(Lithographic Printing Plate Precursor)

A lithographic printing plate precursor of the present invention has an image-recording layer including the compound represented by Formula (1) (Component A), the binder polymer (Component B), the polymerization initiator (Component C), and the polymerizable compound (Component D) on a support.

In addition, the lithographic printing plate precursor of the present invention preferably has an image-recording layer consisting of the infrared-sensitive color developing composition.

In the lithographic printing plate precursor of the present, it is possible to provide an undercoat layer between the support and the image-recording layer and a protective layer on the image-recording layer as necessary.

In addition, the lithographic printing plate precursor of the present invention can be preferably used as on-machine development-type lithographic printing plate precursors on which a development process can be carried out on printers.

Hereinafter, constituent elements of the lithographic printing plate precursor will be described.

<Image-Recording Layer>

For the image-recording layer in the lithographic printing plate precursor, development aptitude and printing aptitude are required. Therefore, the image-recording layer is capable of further including polymer particles below or other components in addition to the compound represented by Formula (1) (Component A), the binder polymer (Component B), the polymerization initiator (Component C), and the polymerizable compound (Component D).

Preferred aspects of Components A to D in the image-recording layer are identical to the above-described preferred aspects in the infrared-sensitive color developing composition of the present invention.

In addition, the preferred content thereof in the image-recording layer are as described above.

—Polymer Particles—

In order to improve the on-machine developing properties of the lithographic printing plate precursor, polymer particles can be used for the image-recording layer. The polymer particles in the present invention are preferably polymer particles capable of converting the image-recording layer to be hydrophobic when irradiated with heat. The polymer particles are preferably at least one selected from hydrophobic thermoplastic polymer particles, thermally reactive polymer particles, polymer particles having polymerizable groups, microcapsules including hydrophobic compounds, and micro gels (crosslinking polymer particles). Among these, polymer particles having polymerizable groups and micro gels are preferred.

Preferred examples of the hydrophobic thermoplastic polymer particles that are used in the present invention include hydrophobic thermoplastic polymer particles described in Research Disclosure No. 33303 of January 1992 and the specifications of JP1997-123387A (JP-H09-123387A, JP1997-131850A (JP-H09-131850A), JP1997-171249A (JP-H09-171249A), JP1997-171250A (JP-H09-171250A), and EU931647B.

Specific examples of polymers that constitute the hydrophobic thermoplastic polymer particles include homopolymers or copolymers of monomers of ethylene, styrene, vinyl chloride, methyl acrylate, ethyl acrylate, methyl methacrylate, ethyl methacrylate, vinylidene chloride, acrylonitrile, vinylcarbazole, acrylates or methacrylates having polyalkylene structures, and the like and mixtures thereof. Preferred examples thereof include copolymers having polystyrene, styrene, and acrylonitrile and methyl polymethacrylate. The average particle diameter of the hydrophobic thermoplastic polymer particles is preferably in a range of 0.01 µm to 2.0 µm.

Examples of the thermally reactive polymer particles that are used in the present invention include polymer fine particles having thermally reactive groups. Polymer particles having thermally reactive groups form hydrophobilized regions through crosslinking by thermal reactions and changes in functional groups at this time.

The thermally reactive groups in the polymer particles having thermally reactive groups may be functional groups that cause any reactions as long as chemical bonds are formed, but are preferably polymerizable groups. Preferred examples thereof include ethylenic unsaturated groups that cause radical polymerization reactions (for example, acryloyl groups, methacryloyl groups, vinyl groups, allyl groups, and the like), cationic polymerizable groups (for example, vinyl groups, vinyloxy groups, epoxy groups, oxetanyl groups, and the like), isocyanato groups that cause addition reactions or blocked bodies thereof, epoxy groups, vinyloxy groups, functional groups having active hydrogen atoms that are reaction partners thereof (for example, amino groups, hydroxy groups, carboxy groups, and the like), carboxy groups that cause condensation reactions, hydroxy groups or amino groups that are reaction partners, acid anhydrides that cause ring-opening addition reactions, amino groups or hydroxy groups which are reaction partners, and the like.

Examples of the microcapsules that are used in the present invention include microcapsules including all or part of the constituent components of the image-recording layer as described in JP2001-277740A and JP2001-277742A. The constituent components of the image-recording layer can also be added outside the microcapsules. A preferred aspect of the image-recording layer including the microcapsules is an image-recording layer including hydrophobic constituent components in the microcapsules and including hydrophilic constituent components outside the microcapsules.

In the present invention, an aspect including crosslinking polymer particles, that is, micro gels can also be used. Micro gels are capable of containing some of the constituent components of the image-recording layer in at least one of the center and surface thereof, and particularly, an aspect of micro capsules that have radical polymerizable groups on the surfaces and thus turn into reactive micro gels is preferred from the viewpoint of image-recording sensitivity or printing resistance.

As a method for putting the constituent components of the image-recording layer into microcapsules or micro gels, well-known methods can be used.

The average particle diameter of the microcapsules or the micro gels is preferably in a range of 0.01 µm to 3.0 µm, more preferably in a range of 0.05 µm to 2.0 µm, and particularly preferably in a range of 0.10 µm to 1.0 µm. Within this range, favorable resolution and temporal stability can be obtained.

The content of the polymer particles is preferably in a range of 5% by mass to 90% by mass of the total solid contents in the image-recording layer.

—Other Components—

The image-recording layer in the present invention may further include other components as necessary.

(1) Low-Molecular-Weight Hydrophilic Compound

In order to improve on-machine developing properties without degrading printing resistance, the image-recording layer in the present invention may include a low-molecular-weight hydrophilic compound. Meanwhile, the low-molecular-weight hydrophilic compound is preferably a compound having a molecular weight of smaller than 1,000, more preferably a compound having a molecular weight of smaller than 800, and still more preferably a compound having a molecular weight of smaller than 500.

As the low-molecular-weight hydrophilic compound, examples of water-soluble organic compounds include glycols such as ethylene glycol, diethylene glycol, triethylene glycol, propylene glycol, dipropylene glycol, and tripropylene glycol and ethers or ester derivatives thereof, polyols such as glycerin, pentaerythritol, and tris(2-hydroxyethyl) isocyanurate, organic amines such as triethanolamine, diethanolamine, and monoethanolamine and salts thereof, organic sulfonic acids such as alkyl sulfonic acid, toluenesulfonic acid, and benzenesulfonic acid and salts thereof, organic sulfamic acids such as alkyl sulfamate and salts thereof, organic sulfuric acids such as alkyl sulfates and alkyl ether sulfates and salts thereof, organic phosphonic acids such as phenylphosphonic acid and salts thereof, organic carboxylic acids such as tartaric acid, oxalic acid, citric acid, malic acid, lactic acid, gluconic acid, and amino acid and salts thereof, betaines, and the like.

In the present invention, it is preferable to add at least one selected from polyols, organic sulfates, organics sulfonates, and betaines.

Specific examples of the organic sulfonates include alkyl sulfonates such as sodium n-butyl sulfonate, sodium n-hexyl sulfonate, sodium 2-ethylhexyl sulfonate, sodium cyclohexyl sulfonate, and sodium n-octyl sulfonate; alkyl sulfonates having ethylene oxide chains such as sodium 5,8,11-trioxapentadecane-1-sulfonate, sodium 5,8,11-trioxaheptadecane-1-sulfonate, sodium 13-ethyl-5,8,11-trioxaheptadecane-1-sulfonate, sodium 5,8,11,14-tetraoxatetracosane-1-sulfate; aryl sulfonates such as sodium benzene sulfonate, sodium p-toluenesulfonate, sodium p-hydroxybenzene sulfonate, sodium p-styrene sulfonate, sodium dimethyl isophthalate-5-sulfonate, sodium 1-naphthyl sulfonate, sodium 4-hydroxynaphthyl sulfonate, disodium 1,5-naphthalene disulfonate, and trisodium 1,3,6-naphthalene trisulfonate, compounds described in Paragraphs "0026" to "0031" of JP2007-276454A and Paragraphs "0020" to "0047" of JP2009-154525A, and the like. The salts may be potassium salts or lithium salts.

Examples of the organic sulfates include sulfates of alkyls, alkenyls, alkynyls, aryls, or heterocyclic monoethers such as polyethylene oxides. The number of ethylene oxide units is preferably in a range of 1 to 4, and the salts are preferably sodium salts, potassium salts, or lithium salts. Specific examples thereof include compounds described in Paragraphs "0034" to "0038" of JP2007-276454A.

The betaines are preferably compounds in which the number of carbon atoms in hydrocarbon substituents into nitrogen atoms is in a range of 1 to 5, and specific examples thereof include trimethyl ammonium acetate, dimethyl propyl ammonium acetate, 3-hydroxy-4-trimethyl ammonio butyrate, 4-(1-pyridinio) butyrate, 1-hydroxyethyl-1-imidazolio acetate, trimethyl ammonium methane sulfonate, dimethyl propyl ammonium methane sulfonate, 3-trimethylammonio-1-propane sulfonate, 3-(1-pyridinio)-1-propane sulfonate, and the like.

Since the low-molecular-weight hydrophilic compound has a small structure in hydrophobic portions and barely has surfactant actions, there are no cases in which dampening water permeates exposed portions (image portions) in the image-recording layer and thus the hydrophobic properties or membrane strength of the image portions degrade, and it is possible to favorably maintain the ink-receiving properties or printing resistance of the image-recording layer.

The amount of the low-molecular-weight hydrophilic compound added to the image-recording layer is preferably in a range of 0.5% by mass to 20% by mass, more preferably in a range of 1% by mass to 15% by mass, and still more preferably in a range of 2% by mass to 10% by mass of the total solid content of the image-recording layer. Within this range, favorable on-machine developing-properties and printing resistance can be obtained.

The low-molecular-weight hydrophilic compound may be used singly or two or more low-molecular-weight hydrophilic compound may be used in a mixed form.

(2) Sensitization Agent

In order to improve ink-absorbing properties, it is possible to use a sensitization agent such as a phosphonium compound, a nitrogen-containing low-molecular-weight compound, or an ammonium group-containing polymer in the image-recording layer. Particularly, in a case in which an inorganic lamellar compound is added to the protective layer, these compounds function as surface coating agents for the inorganic lamellar compound and prevent the ink-absorbing properties from being degraded in the middle of printing due to the inorganic lamellar compound.

Among these, a phosphonium compound, a nitrogen-containing low-molecular-weight compound, and an ammonium group-containing polymer are preferably jointly used as the sensitization agent, and a phosphonium compound, quaternary ammonium salts, and an ammonium group-containing polymer are more preferably jointly used.

Examples of a preferred phosphonium compound include phosphonium compounds described in JP2006-297907A and JP2007-50660A. Specific examples thereof include tetrabutylphosphonium iodide, butyltriphenylphosphonium bromide, tetraphenylphosphonium bromide, 1,4-bis(triphenylphosphonio)butane=di(hexafluorophosphate), 1,7-bis(triphenylphosphonio)heptane=sulfate, 1,9-bis(triphenylphosphonio)nonane=naphthalene-2,7-disulfonate, and the like.

Examples of the nitrogen-containing low-molecular-weight compound include amine salts and quaternary ammonium salts. In addition, examples thereof include imidazolinium salts, benzo imidazolinium salts, pyridinium salts, and quinolinium salts. Among these, quaternary ammonium salts and pyridinium salts are preferred. Specific examples thereof include tetramethylammonium=hexafluorophosphate, tetrabutylammonium=hexafluorophosphate, dodecyltrimethylammonium=p-toluene sulfonate, benzyltriethylammonium=hexafluorophosphate, benzyldimethyloctylammonium=hexafluorophosphate, benzyldimethyldodecylammonium=hexafluorophosphate, compounds described in Paragraphs "0021" to "0037" of JP2008-284858A and Paragraphs "0030" to "0057" of JP2009-90645A, and the like.

As the ammonium group-containing polymer, any ammonium group-containing polymers may be used as long as the groups have ammonium groups in the structures, but polymers including 5% by mol to 80% by mol of (meth)acrylate having ammonium groups in side chains as copolymerization components are preferred. Specific examples thereof include polymers described in Paragraphs "0089" to "0105" of JP2009-208458A.

In the ammonium group-containing polymer, the value of the reducing specific viscosity (unit: ml/g) obtained using the measurement method described in JP2009-208458A is preferably in a range of 5 to 120, more preferably in a range of 10 to 110, and particularly preferably in a range of 15 to 100. In a case in which the reducing specific viscosity is converted to the mass-average molar mass (Mw), the mass-average molar mass is preferably in a range of 10,000 to 150,000, more preferably in a range of 17,000 to 140,000, and particularly preferably in a range of 20,000 to 130,000.

Hereinafter, specific examples of the ammonium group-containing polymer will be described.

(1) 2-(Trimethylammonio)ethyl methacrylate=p-toluenesulfonate/3,6-dioxaheptyl methacrylate copolymer (molar ratio: 10/90, Mw: 45,000)

(2) 2-(Trimethylammonio)ethyl methacrylate=hexafluorophosphate/3,6-dioxaheptyl methacrylate copolymer (molar ratio: 20/80, Mw: 60,000)

(3) 2-(Ethyldimethylammonio)ethyl methacrylate-p-toluenesulfonate/hexyl methacrylate copolymer (molar ratio: 30/70, Mw: 45,000)

(4) 2-(Trimethylammonio)ethyl methacrylate=hexafluorophosphate/2-ethylhexyl methacrylate copolymer (molar ratio: 20/80, Mw: 60,000)
(5) 2-(Trimethylammonio)ethyl methacrylate=methylsulfate/hexyl methacrylate copolymer (molar ratio: 40/60, Mw: 70,000)
(6) 2-(Butyldimethylammonio)ethyl methacrylate=hexafluorophosphate/3,6-dioxaheptyl methacrylate copolymer (molar ratio: 25/75, Mw: 65,000)
(7) 2-(Butyldimethylammonio)ethyl acrylate=haxafluorophosphate/3,6-dioxaheptyl methacrylate copolymer (molar ratio: 20/80, Mw: 65,000)
(8) 2-(Butyldimethylammonio)ethyl methacrylate=13-ethyl-5,8,11-trioxa-1-heptadecanesulfonate/3,6-dioxaheptyl methacrylate copolymer (molar ratio: 20/80, Mw: 75,000)
(9) 2-(Butyldimethylammonio)ethyl methacrylate=haxafluorophosphate/3,6-dioxaheptyl methacrylate/2-hydroxy-3-methacroyloxypropyl methacrylate copolymer (molar ratio: 15/80/5, Mw: 65,000)

The content of the sensitization agent is preferably in a range of 0.01% by mass to 30.0% by mass, more preferably in a range of 0.1% by mass to 15.0% by mass, and still more preferably in a range of 1% by mass to 10% by mass of the total solid content in the image-recording layer.

(3) Surfactant

In order to accelerate developing properties and improve coated surface states, the image-recording layer preferably includes a surfactant.

Examples of the surfactant include nonionic surfactants, anionic surfactants, cationic surfactants, amphoteric surfactants, fluorine-based surfactants, and the like.

Examples of preferred surfactants include fluorine-based surfactants having perfluoroalkyl group in the molecule. Examples of the above-described fluorine-based surfactants include anionic fluorine-based surfactants such as perfluoroalkyl carboxylate, perfluoroalkyl sulfonate, and perfluoroalkyl phosphoric acid esters; amphoteric fluorine-based surfactants such as perfluoroalkyl betaine; cationic fluorine-based surfactants such as perfluoroalkyl trimethylammonium salts; nonionic fluorine-based surfactants such as perfluoroalkyl amine oxide, perfluoroalkyl ethylene oxide adducts, oligomers having perfluoroalkyl groups and hydrophilic groups, oligomers having perfluoroalkyl groups and lipophilic groups, oligomers having perfluoroalkyl groups, hydrophilic groups, and lipophilic groups, urethanes having perfluoroalkyl groups and lipophilic groups. In addition, preferred examples thereof also include fluorine-based surfactants described in JP1987-170950A (JP-S62-170950A), JP1987-226143A (JP-S62-226143A), and JP1985-168144A (JP-S60-168144A).

The surfactant can be used singly or two or more surfactants can be used in a combined form.

The content of the surfactant is preferably in a range of 0.001% by mass to 10% by mass and more preferably in a range of 0.01% by mass to 5% by mass of the total solid content in the image-recording layer.

(4) Others

Furthermore, to the image-recording layer, as other components, it is possible to add a surfactant, a colorant, a printing-out agent, a polymerization inhibitor, higher aliphatic acid derivatives, a plasticizer, inorganic particles, inorganic lamellar compounds, a co-sensitizing agent, and/or a chain transfer agent. Specifically, it is preferable to use compounds and amounts thereof added described in Paragraphs "0114" to "0159" of JP2008-284817A, Paragraphs "0023" to "0027" of JP2006-091479A, and Paragraph "0060" of US2008/0311520A.

—Formation of Image-Recording Layer—

The image-recording layer in the lithographic printing plate precursor of the present invention is formed by, for example, as described in Paragraphs "0142" and "0143" of JP2008-195018A, dispersing or dissolving the necessary components described above in a well-known solvent so as to prepare a coating fluid, applying the coating fluid onto a support using a well-known method such as bar coating, and drying the coating fluid. The coating amount (solid content) of the image-recording layer on the support which is obtained after application and drying varies depending on applications, but is preferably in a range of 0.3 g/m$^2$ to 3.0 g/m$^2$. Within this range, a favorable sensitivity and favorable membrane characteristics of the image-recording layer can be obtained.

<Undercoat Layer>

In the lithographic printing plate precursor of the present invention, an undercoat layer (in some cases, referred to as the interlayer) is preferably provided between the image-recording layer and the support. The undercoat layer strengthens adhesiveness between the support and the image-recording layer in exposed portions and facilitates peeling the support and the image-recording layer in non-exposed portions, and thus the undercoat layer contributes to improving developing properties without impairing printing resistance. In addition, in the case of exposure using infrared lasers, the undercoat layer functions as an adiabatic layer and thus has an effect of preventing the sensitivity from being degraded due to the diffusion of heat generated by exposure in the support.

Examples of compounds that can be used for the undercoat layer include polymers having adsorbent groups that can be adsorbed to the surface of the support and hydrophilic groups. In order to improve adhesiveness to the image-recording layer, polymers having adsorbent groups and hydrophilic groups and further having crosslinking groups are preferred. The compounds that can be used for the undercoat layer may be low-molecular-weight compounds or high-molecular-weight polymers. The compounds that can be used for the undercoat layer may be used in a mixed form of two or more kinds as necessary.

In a case in which the compounds that are used for the undercoat layer are polymers, copolymers of monomers having adsorbent groups, monomers having hydrophilic groups, and monomers having crosslinking groups are preferred.

The adsorbent groups that can be adsorbed to the surface of the support are preferably phenolic hydroxy groups, carboxy groups, —PO$_3$H$_2$, —OPO$_3$H$_2$, —CONHSO$_2$—, —SO$_2$NHSO$_2$—, —COCH$_2$COCH$_3$. The hydrophilic groups are preferably sulfo groups or salts thereof and salts of carboxy groups. The crosslinking groups are preferably methacryl groups, allyl groups, and the like.

The polymers may have crosslinking groups introduced due to the formation of salts between polar substituents of the polymers and compounds having substituents having opposite charges of the above-described polar substituents and ethylenic unsaturated bonds and may be further copolymerized with monomers other than the above-described monomers, preferably, hydrophilic monomers.

Specifically, preferred examples thereof include silane coupling agents having ethylenic double bond reactive groups that are capable of addition polymerization described in JP1998-282679A (JP-H10-282679A) and phosphorus compounds having ethylenic double bond reactive groups described in JP 1990-304441A (JP-H02-304441A). Low-molecular-weight or high-molecular-weight compounds having crosslinking groups (preferably ethylenic unsaturated bond groups), functional groups that interact with the surface of the support, and hydrophilic groups described in JP2005-238816A, JP2005-125749A, JP2006-239867A, and JP2006-215263A are also preferably used.

More preferred examples thereof include high-molecular-weight polymers having adsorbent groups that can be adsorbed to the surface of the support, hydrophilic groups, and crosslinking groups described in JP2005-125749A and JP2006-188038A.

The content of ethylenic unsaturated bonds in the polymer for the undercoat layer is preferably in a range of 0.1 mmol to 10.0 mmol and more preferably in a range of 0.2 mmol to 5.5 mmol per gram of the polymer.

The mass-average molar mass (the weight-average molecular weight, Mw) of the polymer for the undercoat layer is preferably 5,000 or higher and more preferably in a range of 10,000 to 300,000.

In addition to the above-described compounds for the undercoat layer, the undercoat layer may also include a chelate agent, secondary or ternary amines, a polymerization inhibitor, compounds having amino groups or functional groups having a polymerization-inhibiting function and groups that interact with the surfaces of aluminum supports (for example, 1,4-diazabicyclo[2.2.2]octane (DABCO), 2,3,5,6-tetrahydroxy-p quinone, chloranil, sulfophthalic acid, hydroxyethyl ethylene diamine triacetic acid, dihydroxyethyl ethylenediamine diacetic acid, hydroxyethyl iminodiacetic acid, and the like), and the like in order to prevent contamination over time.

The undercoat layer is formed using well-known coating methods. The coating amount (solid content) of the undercoat layer is preferably in a range of 0.1 mg/m$^2$ to 100 mg/m$^2$ and more preferably in a range of 1 mg/m$^2$ to 30 mg/m$^2$.

<Protective Layer>

In the lithographic printing plate precursor of the present invention, a protective layer (in some cases, also referred to as the overcoat layer) is preferably provided on the image-recording layer. The protective layer has a function of suppressing image formation-inhibiting reactions caused by the shielding of oxygen and additionally has a function of preventing the generation of damage in the image-recording layer and abrasion prevention during exposure using high-luminance lasers.

Protective layers having the above-described characteristics are described in, for example, the specification of U.S. Pat. No. 3,458,311A and JP1980-49729B (JP-S55-49729B). As poor oxygen-transmissible polymers that can be used for the protective layer, it is possible to appropriately select and use any one of water-soluble polymers and water-insoluble polymers, and, if necessary, it is also possible to use two or more polymers in a mixed form. Specific examples thereof include polyvinyl alcohols, modified polyvinyl alcohols, polyvinyl pyrrolidone, water-soluble cellulose derivatives, poly(meth)acrylonitrile, and the like.

As the modified polyvinyl alcohols, acid-modified polyvinyl alcohols having carboxy groups or sulfo groups are preferably used. Specific examples thereof include modified-polyvinyl alcohols described in JP2005-250216A and JP2006-259137A.

The protective layer in the present invention preferably includes inorganic lamellar compounds in order to enhance oxygen-shielding properties. The inorganic lamellar compounds refer to particles having thin flat plate shapes, and examples thereof include mica groups such as natural mica and synthetic mica, talc represented by Formula 3MgO.4SiO.H$_2$O, taeniolite, montmorillonite, saponite, hectorite, zirconium phosphate, and the like.

The inorganic lamellar compounds that can be preferably used in the present invention are mica compounds. Examples of mica compounds include mica groups such as natural mica and synthetic mica represented by Formula: A(B, C)$_{2-5}$D$_4$O$_{10}$(OH, F, O)$_2$ [here, A is any one of K, Na, and Ca, B and C are any of Fe (II), Fe (III), Mn, Al, Mg, and V, and D is Si or Al.].

In the mica groups, examples of natural mica include white mica, soda mica, gold mica, black mica, and lepidolite. Examples of synthetic mica include non-swelling mica such as fluorphlogopite KMg$_3$(AlSi$_3$O$_{10}$) F$_2$, potassium tetrasilic mica KMg$_{2.5}$Si$_4$O$_{10}$)F$_2$, and, Na tetrasilylic mica NaMg$_{2.5}$(Si$_4$O$_{10}$)F$_2$, swelling mica such as Na or Li taeniolite (Na, Li)Mg$_2$Li(Si$_4$O$_{10}$)F$_2$, montmorillonite-based Na or Li hectorite (Na, Li)$_{1/8}$Mg$_{2/5}$Li$_{1/9}$(Si$_4$O$_{10}$)F$_2$, and the like. Furthermore, synthetic smectite is also useful.

In the present invention, among the above-described mica compounds, fluorine-based swelling mica is particularly useful. That is, swelling synthetic mica has a laminate structure consisting of unit crystal lattice layers having a thickness in a range of approximately 10 angstroms to 15 angstroms, and metal atoms are more actively substituted than in any other clay minerals. As a result, positive charges are deficient in the lattice layers, and positive ions such as Li$^+$, Na$^+$, Ca$^{2+}$, and Mg$^{2+}$ are adsorbed between the layers in order to compensate for the deficiency. Positive ions interposed between the layers are referred to as exchangeable positive ions and are exchanged with various positive ions. Particularly, in a case in which the positive ions between the layers are Li$^+$ and Na$^+$, the ionic radii are small, and thus the bonds between lamellar crystal lattices are weak, and mica is significantly swollen by water. When shear is applied in this state, mica easily cleavages and forms a stable sol in water. The above-described tendency of swelling synthetic mica is strong, and the swelling synthetic mica is particularly preferably used in the present invention.

From the viewpoint of diffusion control, regarding the shapes of the mica compounds, the thickness is preferably thin, and the planar size is preferably large as long as the smoothness and active light ray-transmitting properties of coated surfaces are not impaired. Therefore, the aspect ratio is preferably 20 or higher, more preferably 100 or higher, and particularly preferably 200 or higher. Meanwhile, the aspect ratio is the ratio of the long diameter to the thickness of a particle and can be measured from projection views obtained from the microphotograph of the particle. As the aspect ratio increases, the obtained effect becomes stronger.

Regarding the particle diameters of the mica compound, the average long diameter thereof is preferably in a range of 0.3 μm to 20 μm, more preferably in a range of 0.5 μm to 10 μm, and particularly preferably in a range of 1 μm to 5 μm. The average thickness of the particles is preferably 0.1 μm or smaller, more preferably 0.05 μm or smaller, and particularly preferably 0.01 μm or smaller. Specifically, for example, in the case of swelling synthetic mica which is a typical compound, a preferred aspect has a thickness in a range of 1 nm to 50 nm and a surface size (long diameter) in a range of approximately 1 μm to 20 μm.

The content of the inorganic lamellar compound is preferably in a range of 0% by mass to 60% by mass and more preferably in a range of 3% by mass to 50% by mass of the total solid content of the protective layer. Even in a case in which multiple kinds of inorganic lamellar compounds are jointly used, the total amount of the inorganic lamellar compounds is preferably the above-described mass. Within the above-described range, the oxygen-shielding properties improve, and a favorable sensitivity can be obtained. In addition, the degradation of the ink-absorbing properties can be prevented.

The protective layer may include well-known additives such as a plasticizer for imparting flexibility, a surfactant for improving coating properties, and inorganic fine particles that control sliding properties on the surface. In addition, it is also possible to add the sensitization agent described in the section of the image-recording layer to the protective layer.

The protective layer is formed using a well-known coating method. Regarding the coating amount of the protective layer, the coating amount after drying is preferably in a range of 0.01 g/m² to 10 g/m², more preferably in a range of 0.02 g/m² to 3 g/m², and particularly preferably in a range of 0.02 g/m² to 1 g/m².

<Support>

Supports that can be used in the lithographic printing plate precursor of the present invention are not particularly limited, and examples thereof include well-known supports for lithographic printing plate precursors. The support is preferably an aluminum plate which has been roughened using a well-known method and anode-oxidized.

On the aluminum plate, as necessary, it is possible to appropriately select and carry out enlargement processes or sealing processes of micropores in anode oxide films described in JP2001-253181A and JP2001-322365A, surface hydrophilization processes using alkali metal silicate as described in the specifications of U.S. Pat. No. 2,714,066A, U.S. Pat. No. 3,181,461A, U.S. Pat. No. 3,280,734A, and U.S. Pat. No. 3,902,734A, and surface hydrophilization processes using polyvinyl phosphate or the like as described in the specifications of U.S. Pat. No. 3,276,868A, U.S. Pat. No. 4,153,461A, and U.S. Pat. No. 4,689,272A.

In the support, the center line average roughness is preferably in a range of 0.10 µm to 1.2 µm.

To the support, as necessary, it is possible to provide a backcoat layer including organic polymer compounds described in JP1993-45885A (JP-H05-45885A) or alkoxy compounds of silicon described in JP1994-35174A (JP-H06-35174A) on the surface opposite to the surface on which the image-recording layer is formed.

(Lithographic Printing Plate and Production Method Therefor)

A lithographic printing plate of the present invention is a lithographic printing plate made of the lithographic printing plate precursor of the present invention.

A plate making method for a lithographic printing plate of the present invention is not particularly limited, but preferably includes a preparation step of preparing the lithographic printing plate precursor of the present invention, an exposure step of exposing the lithographic printing plate precursor in an image pattern, and an on-machine development process step of removing non-image portions by supplying printing ink and dampening water to the lithographic printing plate precursor that has been exposed in an image pattern on a printer.

<Preparation Step>

The plate making method for a lithographic printing plate precursor of the present invention preferably includes a preparation step of preparing the lithographic printing plate precursor of the present invention.

In the preparation step, there are no particular limitations except for the preparation of the lithographic printing plate precursor of the present invention, and the preparation step may be a step of preparing the lithographic printing plate precursor of the present invention which is separated produced or a step of producing the lithographic printing plate precursor of the present invention.

<Exposure Step>

The plate making method for a lithographic printing plate precursor of the present invention preferably includes an exposure step of exposing the lithographic printing plate precursor of the present invention in an image pattern.

The lithographic printing plate precursor of the present invention can be exposed in an image pattern using a method in which digital data is scanned and exposed using infrared lasers.

The wavelength of the light source that is used is preferably in a range of 750 nm to 1,400 nm. The light source having a wavelength in a range of 750 nm to 1,400 nm is preferably a solid laser or a semiconductor laser that radiates infrared rays. The exposure mechanism may be any one of in-plane drum methods, external surface drum methods, flat head methods, and the like.

The exposure step can be carried out using platesetters or the like and well-known methods. In addition, exposure may be carried out on a printer using a printer including an exposure device after the lithographic printing plate precursor is mounted on the printer.

<On-Machine Development Process Step>

In the on-machine development process step, when printing is carried out on the lithographic printing plate precursor that has been exposed in an image pattern by supplying printing ink and dampening water without carrying out any development processes thereon, non-exposed portions on the lithographic printing plate precursor are removed at the initial stage of printing, and accordingly, the hydrophilic surface of the support is exposed, and non-image portions are formed. As the printing ink and the dampening water, well-known printing ink and dampening water for lithographic printing are used. Here, any of printing ink and dampening water may be first supplied to the plate surface, but it is preferable to first supply printing ink from the viewpoint of preventing contamination by the components of the image-recording layer from which dampening water is removed.

In the above-described manner, the lithographic printing plate precursor is on-machine-developed on an off-set printer and is used as it is for printing a number of pieces of paper.

The plate making method for a lithographic printing plate of the present invention may include other well-known steps in addition to the above-described steps.

(Compound Represented by Formula (1) and Infrared-Sensitive Color Developer)

The compound represented by Formula (1) is a new compound and can be preferably used as infrared-sensitive color developers.

A preferred aspect of the compound represented by Formula (1) as a new compound is identical to the preferred aspect of the compound represented by Formula (1) in the above-described infrared-sensitive color developing composition of the present invention.

EXAMPLES

Hereinafter, the present invention will be described using examples, but the present invention is not limited thereto. Meanwhile, in the present examples, "parts" and "%" indicate "parts by mass" and "% by mass" unless particularly otherwise described. Meanwhile, specific compounds W-1, W-3 to W-6, W-8, W-9, and W-12, which will be used in the examples, are respectively the same compounds as the above-described compounds W-1, W-3 to W-6, W-8, W-9, and W-12. In addition, Et represents an ethyl group.

Synthesis Example 1: Synthesis of Specific Compound W-1

A synthesis method for a specific compound W-1 will be described below. In addition, the other compounds were also synthesized using the same synthesis method.

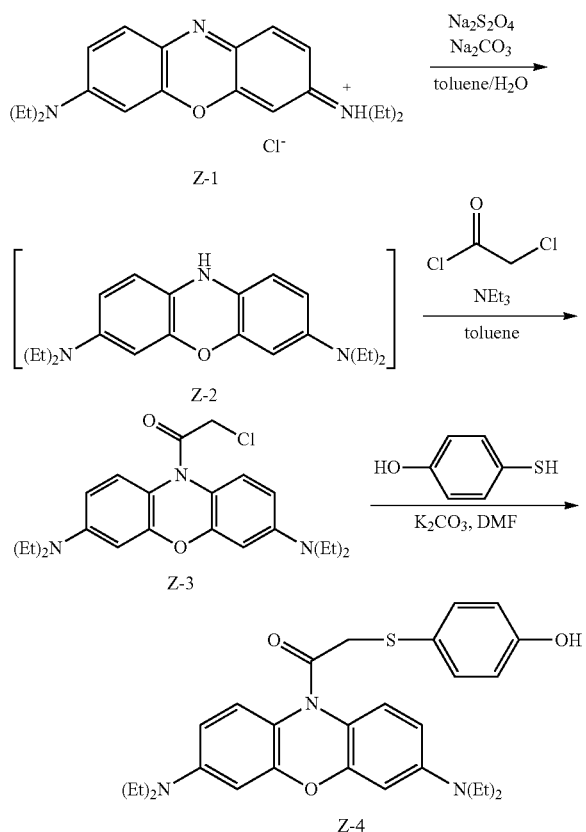

<Preparation of Z-2>

A mixture of Z-1 (7.20 parts, 20.0 molar equivalents), $Na_2S_2O_4$ (10.4 parts, 60.0 molar equivalents), and $Na_2CO_3$ (6.36 parts, 60.0 molar equivalents) was reacted in a biphasic system of toluene (500 parts) and water (500 parts) at room temperature (25° C., which shall apply below) for two hours in a nitrogen flow. A toluene solution obtained by means of a separation operation was rapidly dried and filtered using magnesium sulfate, thereby obtaining a Z-2 solution.

<Synthesis of Z-3>

Chloroacetyl chloride (3.39 parts, 30.0 molar equivalents) was added dropwise to a liquid mixture of the Z-2 solution cooled in an ice bath and triethylamine ($NEt_3$, 3.04 parts, 30.0 molar equivalents) in a nitrogen flow. After the dropwise addition, the mixture was heated up to room temperature and was stirred for 12 hours. After that, water was added thereto, an organic layer was washed with water (500 parts) three times and was dried using magnesium sulfate. A solid obtained by distilling the organic layer was recrystallized using ethanol/hexane, thereby obtaining Z-3 (3.92 parts, 9.77 molar equivalents).

$^1$H-NMR (300 MHz, heavy dimethyl sulfoxide) δ=1.09 (q, 12H), 3.38 (t, 8H), 4.58 (s, 2H), 6.38-6.48 (m, 4H) 7.36 (d, 2H)

<Synthesis of Z-4>

Z-3 (3.00 parts, 7.47 molar equivalents), 4-mercaptophenol (0.942 parts, 7.47 molar equivalents), and potassium carbonate ($K_2CO_3$, 2.07 parts, 16.1 molar equivalents) were stirred in dimethyl formamide (DMF, 30 parts) at room temperature for 30 minutes. After ethyl acetate (100 parts) and an aqueous solution of saturated ammonium chloride (100 parts) were added to the reaction liquid, the organic layer was further washed with water (100 g) and then was dried using magnesium sulfate. A solid obtained by distilling the solvent of the organic layer was washed with ethyl acetate/hexane, thereby obtaining Z-4 (1.75 parts, 3.56 molar equivalents).

$^1$H-NMR (300 MHz, heavy dimethyl sulfoxide) δ=1.09 (t, 12H), 3.38 (q, 8H), 3.94 (s, 2H), 6.37-6.47 (m, 4H) 6.64-6.69 (m, 2H), 7.14-7.19 (m, 2H), 7.31 (d, 2H)

<Synthesis of Specific Compound W-1>

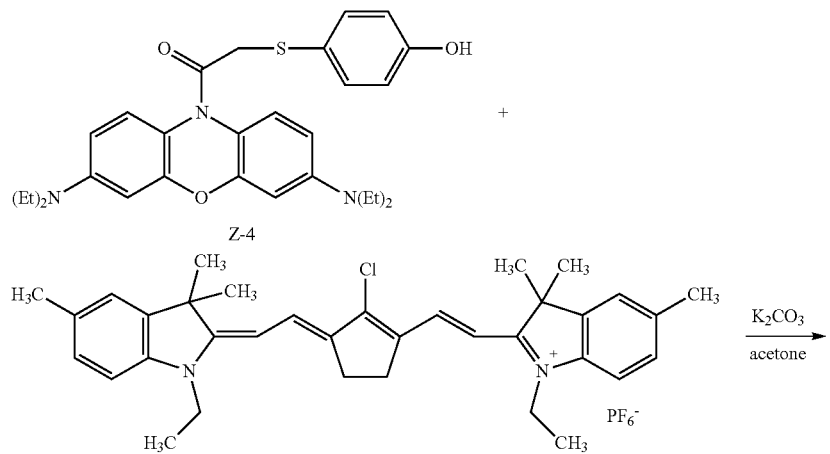

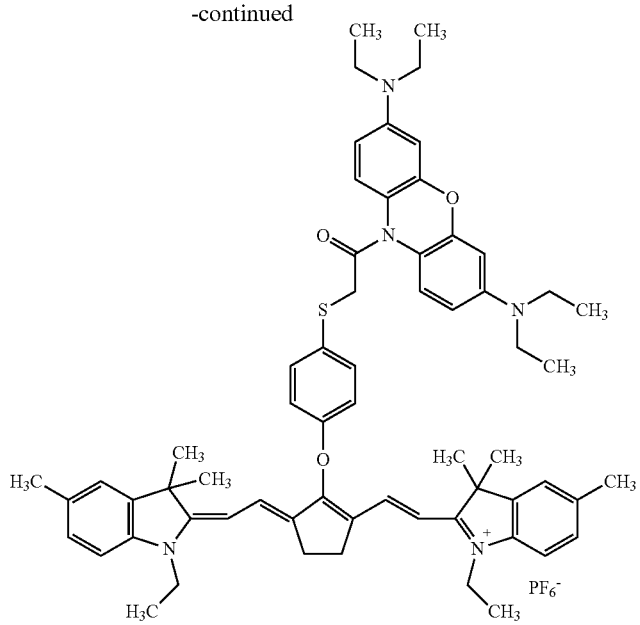

W-1

According to the above-described synthesis scheme, an IR dye (Z-5) (2.31 parts, 3.00 molar equivalents), Z-4 (1.47 parts, 3.00 molar equivalents), and potassium carbonate (0.483 parts, 3.49 molar equivalents) were stirred in an acetone solution (10 parts) at room temperature for one hour. After water (100 parts) and ethyl acetate (20 parts) were added thereto, the obtained solid was filtered. The filtrate was washed with water, thereby obtaining a specific compound W-1 (2.32 parts, 2.06 molar equivalents).

The structure of the obtained specific compound W-1 was identified by means of NMR. The measurement result will be described below.

$^1$H-NMR (300 MHz, heavy dimethyl sulfoxide) δ=1.09 (t, 12H), 1.24 (t, 6H), 1.99 (s, 12H), 2.10 (s, 6H), 2.86 (br, 4H), 3.32 (t, 8H), 3.94 (s, 2H), 4.10 (q, 4H), 5.90 (d, 2H), 6.36-6.45 (m, 4H), 6.64-6.69 (m, 2H), 7.11-7.47 (m, 12H)

Examples 1 to 9 and Comparative Examples 1 and 2

Evaluation of Infrared-Sensitive Color Developing Compositions

I. Infrared-Sensitive Color Developing Composition Films

I-1. Production of Infrared-Sensitive Color Developing Composition Films A-1 to A-9

The following infrared-sensitive color developing composition solution (1) was prepared, was applied onto a 0.18 mm-thick polyester film by means of bar coating so that the dried coating amount reached 1.0 g/m$^2$, and then was dried in an oven at 100° C. for 60 seconds, thereby producing infrared-sensitive color developing composition films A-1 to A-9 (for Examples 1 to 9).

<Infrared-Sensitive Color Developing Composition Solution (1)>
Polymethyl methacrylate (Mw: 12,000): 0.636 parts
Specific compound (the compound shown in Table 1): 0.015 parts
Onium salt [the following structure]: the amount shown in Table 1
Fluorine-based surfactant [the following structure]: 0.008 parts
2-Butanone: 9.700 parts The structures of the onium salt and the fluorine-based surfactant described above will be illustrated below. Meanwhile, the numeric values 30 and 70 at the bottom right of the parentheses of the following fluorine-based surfactant represent molar ratios, and, in addition, the numeric values at the bottom right of the parentheses of the alkyleneoxy structure represent repeating numbers.

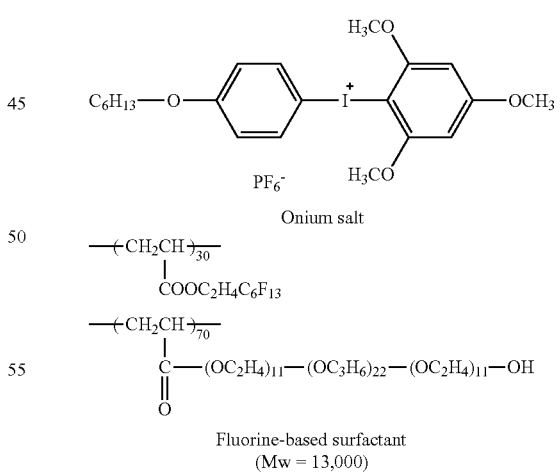

Onium salt

Fluorine-based surfactant (Mw = 13,000)

I-2. Production of Infrared-Sensitive Color Developing Composition A'-1

The following infrared-sensitive color developing composition solution (2) was prepared, was applied onto a 0.18 mm-thick polyester film by means of bar coating so that the dried coating amount reached 1.0 g/m$^2$, and then was dried in an oven at 100° C. for 60 seconds, thereby producing an infrared-sensitive color developing composition film A'-1 [for Comparative Example 1].

<Infrared-Sensitive Color Developing Composition Solution (2)>

Polymethyl methacrylate (Mw: 12,000): 0.636 parts
Infrared-absorbing dye [the following structure]: 0.020 parts
Onium salt [the above structure]: the amount shown in Table 1
Fluorine-based surfactant [the above structure]: 0.008 parts
2-Butanone: 9.700 parts The structures of the infrared-absorbing dye described above will be illustrated below.

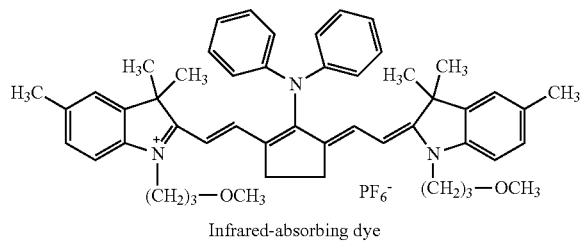

Infrared-absorbing dye

I-3. Production of Infrared-Sensitive Color Developing Composition A'-2

The following infrared-sensitive color developing composition solution (3) was prepared, was applied onto a 0.18 mm-thick polyester film by means of bar coating so that the dried coating amount reached 1.0 g/m², and then was dried in an oven at 100° C. for 60 seconds, thereby producing an infrared-sensitive color developing composition film A'-2 [for Comparative Example 2].

<Infrared-Sensitive Color Developing Composition Solution (3)>

Polymethyl methacrylate (Mw: 12,000): 0.636 parts
Infrared-absorbing dye [the above structure]: 0.020 parts
Comparative compound [the following structure]: 0.030 parts
Onium salt [the above structure]: the amount shown in Table 1
Fluorine-based surfactant [the above structure]: 0.008 parts
2-Butanone: 9.700 parts The structures of the comparative compound described above will be illustrated below.

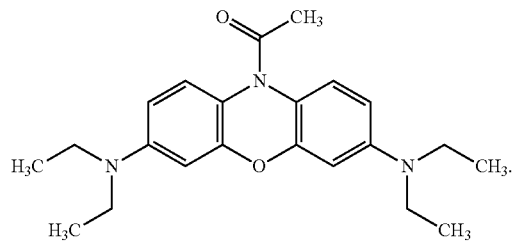

Comparative Compound

I-4. Evaluation of Color-Developing Properties of Infrared-Sensitive Color Developing Composition Film The produced infrared-sensitive color developing composition film was exposed while changing the output in a VIOLET semiconductor laser Vx9600 (InGaN-based semiconductor laser 405 nm±10 nm) manufactured by FUJIFILM electronic Imaging Co., Ltd. at a resolution of 2,483 dpi using 50% square dots as an exposure pattern. Meanwhile, the exposure was carried out under conditions of 25° C. and 50% RH.

In order to evaluate the color-developing properties, color development was measured immediately after the exposure and two hours after the exposure under conditions of a dark plate and room temperature. In addition, the infrared-sensitive color developing composition film was stored for three days under conditions of 60° C. and a humidity of 70% RH, and then color development was measured immediately after the exposure of the color developing composition film that had been forcibly aged. Color development was expressed using the difference ΔL between the L value of an exposed portion and the L value of a non-exposed portion using the L values (brightness) in the L*a*b color specification system. A larger value of ΔL indicates superior color-developing properties. The color-developing properties were measured using a spectrophotometer CM2600d manufactured by Konica Minolta Inc. and operation software CM-S100W by means of a specular component excluded (SCE) method. The results are shown in Table 1.

TABLE 1

| | Infrared-sensitive color developing composition Type | Specific compound Type | Onium salt Added amount (parts) | Color-developing properties (ΔL) | | |
| --- | --- | --- | --- | --- | --- | --- |
| | | | | Immediately after exposure | After two hours | After forcible exposure |
| Example 1 | A-1 | W-1 | Not added | 10 | 10 | 10 |
| Example 2 | A-2 | W-1 | 0.162 | 12 | 12 | 12 |
| Example 3 | A-3 | W-3 | Not added | 10 | 10 | 10 |
| Example 4 | A-4 | W-4 | Not added | 10 | 10 | 10 |
| Example 5 | A-5 | W-5 | Not added | 10 | 10 | 10 |
| Example 6 | A-6 | W-6 | Not added | 10 | 10 | 10 |
| Example 7 | A-7 | W-8 | Not added | 8.5 | 8.5 | 8.5 |
| Example 8 | A-8 | W-9 | Not added | 8.5 | 8.5 | 8.5 |
| Example 9 | A-9 | W-12 | Not added | 8 | 8 | 8 |
| Comparative Example 1 | A'-1 | — | 0.162 | 5 | 2.5 | 2.5 |
| Comparative Example 2 | A'-2 | — | 0.162 | 6 | 3.5 | 3.5 |

From the results in Table 1, the infrared-sensitive color developing composition of the present invention exhibited favorable color-developing properties. Compared with Comparative Example 2 to which an electron donating-type color developer and an infrared absorbent were separately added, the infrared-sensitive color developing composition exhibited more favorable color-developing properties even with small amounts thereof, and thus it was clarified that the color-developing property-improving effect of the compound represented by Formula (1), in which it is assumed that electrons are capable of migrating in the molecule, was extremely strong. In addition, it was clarified that the color-developing properties were improved by adding a polymerization initiator thereto. In addition, it was clarified that, when a compound represented by Formula (3), the color-developing properties were stronger. Furthermore, it was clarified that, when the total number of atoms in $X^1$ in Formula (1) which connected skeletons together was 15 or smaller, the color-developing properties were stronger.

Examples 10 to 18 and Comparative Examples 3 and 4

Evaluation of on-Machine Development-Type Lithographic Printing Plate Precursors II. On-Machine Development-Type Printing Plates II-1. Production of Lithographic Printing Plate Precursors B-1 to B-9

[Production of Support]

In order to remove rolling oil on the surface of a 0.3 mm-thick aluminum plate (material JIS A 1050), a defatting process was carried out thereon using an aqueous solution of 10% by mass of sodium aluminate at 50° C. for 30 seconds, and then, the aluminum surface was grained using three implanted nylon brushes having hair diameters of 0.3 mm and a suspension of pumice having a median diameter of 25 μm and water (specific gravity: 1.1 g/cm$^3$) and well washed with water. This plate was etched by being immersed in an aqueous solution of 25% by mass of sodium hydroxide at 45° C. for nine seconds, was washed with water, then, was further immersed in 20% by mass of nitric acid at 60° C. for 20 seconds, and was washed with water. At this time, the etched amount of the grained surface was approximately 3 g/m$^2$.

Next, an electrochemical roughening process was continuously carried out thereon using alternating-current voltage of 60 Hz. At this time, an electrolytic solution was an aqueous solution of 1% by mass of nitric acid (including 0.5% by mass of aluminum ions), and the liquid temperature was 50° C. The electrochemical roughening process was carried out thereon using an alternating current source waveform in which the time TP taken for the current value to reach the peak from zero was 0.8 msec, a duty ratio of 1:1, a trapezoidal square-wave alternating current, and a carbon electrode as an opposite electrode. As an auxiliary anode, ferrite was used. The current density was 30 A/dm$^2$ in terms of the peak value of the current, and 5% of the current coming from the power supply was divided into the auxiliary positive electrode. Regarding the quantity of electricity during nitric acid electrolysis, the quantity of electricity was 175 C/dm$^2$ when the aluminum plate served as the positive electrode. After that, the plate was washed with water by means of spraying.

Subsequently, an electrochemical roughening process was carried out thereon using the same method as nitric acid electrolysis in an aqueous solution of 0.5% by mass of hydrochloric acid (including 0.5% by mass of aluminum ions) and an electrolytic solution having a liquid temperature of 50° C. under a condition of the quantity of electricity of 50 C/dm$^2$ when the aluminum plate served as the positive electrode, and then, the plate was washed with water by means of spraying.

Next, 2.5 g/m$^2$ of a direct current anode oxide film was provided to this plate at a current density of 15 A/dm$^2$ using 15% by mass of sulfuric acid (including 0.5% by mass of aluminum ions) as an electrolytic solution, and then water washing and drying were carried out thereon, thereby producing a support A.

After that, in order to ensure the hydrophilic properties of non-image portions, a silicate process was carried out on the support A using an aqueous solution of 2.5% by mass of No. 3 sodium silicate at 60° C. for ten seconds, and then the support was washed with water, thereby obtaining a support B. The attached amount of Si was 10 mg/m$^2$. The center line average roughness (Ra) of the support B was measured using a needle having a diameter of 2 μm and was found to be 0.51 μm.

[Formation of Undercoat Layer]

Next, the following coating fluid for the undercoat layer was applied onto the support B so that the dried coating amount reached 20 mg/m$^2$, thereby producing a support having the following undercoat layer.

<Coating Fluid for Undercoat Layer>

Compound for undercoat layer having the following structure: 0.18 parts

Hydroxyethyl iminodiacetic acid: 0.10 parts

Methanol: 55.24 parts

Water: 6.15 parts

Meanwhile, the numeric values at the bottom right of the parentheses representing individual constituent units in the following compound for the undercoat layer represent molar ratios, and, in addition, the parentheses in ethylene oxide groups represent repeating numbers.

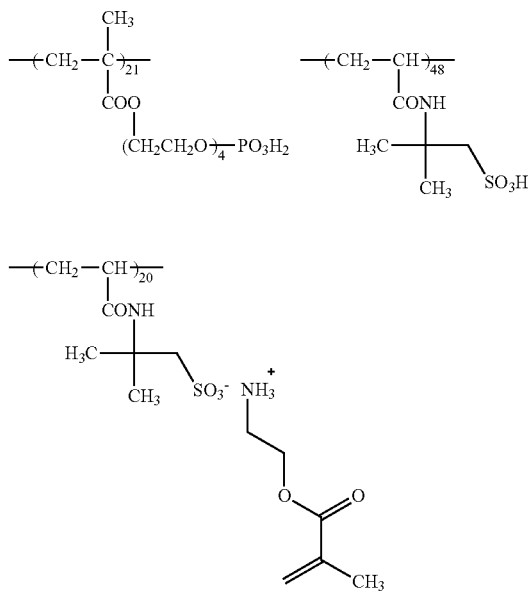

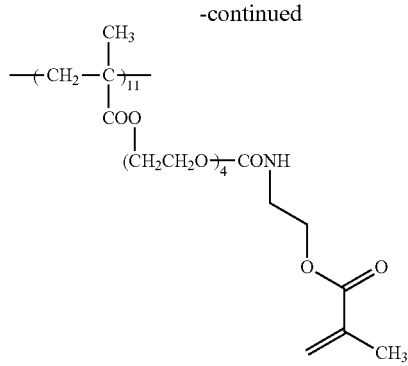

Compound for undercoat layer
(Mw = 100,000)

[Formation of Image-Recording Layer]

A coating fluid for an image-recording layer (1) having the following composition was applied onto the undercoat layer formed in the above-described manner by means of bar coating and then was dried in an oven at 100° C. for 60 seconds, thereby forming an image-recording layer having a dried coating amount of 1.0 g/m².

The coating fluid for the image-recording layer (1) was obtained by mixing and stirring the following photosensitive liquid (1) and a micro gel liquid immediately before the coating.

<Photosensitive Liquid (1)>

Binder polymer [the following structure]: 0.240 parts

Specific compound (the compound shown in Table 2): 0.030 parts

Onium salt (polymerization initiator) [the above structure]: 0.162 parts

Polymerizable compound (tris(acryloyloxyethyl)isocyanurate, NK ester A-9300, manufactured by Shin-Nakamura Chemical Co., Ltd.): 0.192 parts Low-molecular-weight hydrophilic compound (tris(2-hydroxyethyl)isocyanurate): 0.062 parts Low-molecular-weight hydrophilic compound [the following structure]: 0.050 parts Sensitization agent (phosphonium compound, the following structure): 0.055 parts Sensitization agent (benzyl-dimethyl-octylammonium.PF$_6$ salt): 0.018 parts Sensitization agent (ammonium group-containing polymer, the following structure, reducing specific viscosity of 44 ml/g): 0.035 parts Fluorine-based surfactant [the above structure]: 0.008 parts 2-Butanone: 1.091 g 1-Methoxy-2-propanol: 8.609 parts The structures of the low-molecular-weight hydrophilic compound, the phosphonium compound, and the ammonium group-containing polymer are as described below. Meanwhile, the numeric values at the bottom right of the parentheses representing individual constituent units in the following illustrations represent molar ratios, and the parentheses in ethylene oxide groups represent repeating numbers.

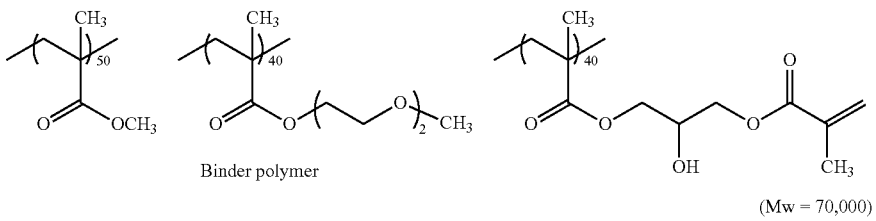

Binder polymer (Mw = 70,000)

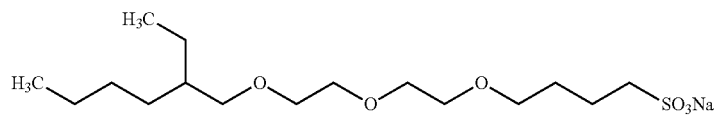

Low-molecular-weight hydrophilic compound

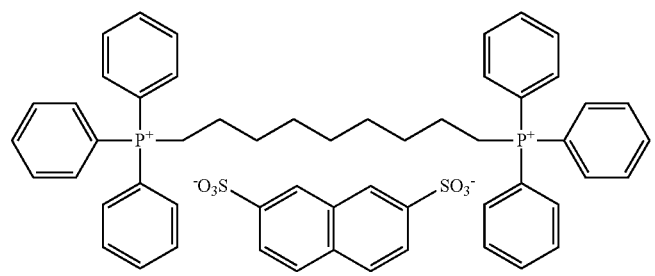

Phosphonium compound

-continued

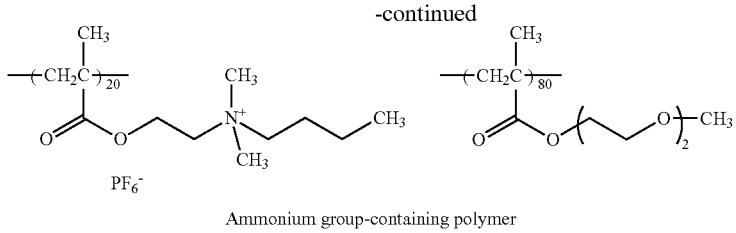

Ammonium group-containing polymer

<Micro Gel Liquid>
Micro gel [the following synthesis method]: 2.640 parts
Distilled water: 2.425 parts
—Synthesis of Micro Gel—
As oil-phase components, trimethylolpropane and xylene diisocyanate adduct (manufactured by Mitsui Chemicals, Inc., TAKENATE D-110N) (10 parts), pentaerythritol triacrylate (manufactured by Nippon Kayaku Co., Ltd., SR444) (3.15 parts), and alkylbenzene sulfonate (manufactured by Takemoto Oil & Fat Co., Ltd., PIONIN A-41C) (0.1 parts) were dissolved in ethyl acetate (17 parts). As a water-phase component, an aqueous solution of 4% by mass of polyvinyl alcohol (40 parts) (PVA-205 manufactured by Kuraray Co., Ltd.) was prepared. The oil-phase components and the water-phase component were mixed together and were emulsified using a homogenizer at 12,000 rmp for 10 minutes. The obtained emulsified substance was added to distilled water (25 parts), the mixture was stirred at room temperature for 30 minutes, and then was stirred at 50° C. for three hours. The concentration of the solid contents of the micro gel liquid obtained in the above-described manner was diluted using distilled water so as to reach 15% by mass, and this micro gel liquid was used as the micro gel. The average particle diameter of the micro gel was measured using a light scattering method and was found to be 0.2 μm.

[Formation of Protective Layer]
A protective layer coating liquid having the following composition was further applied onto the image-recording layer by means of bar coating and then was dried in an oven at 120° C. for 60 seconds, thereby forming a protective layer having a dried coating amount of 0.15 g/m² and thus obtaining lithographic printing plate precursors B-1 to B-9 (for Examples 10 to 18).

<Protective Layer Coating Liquid>
Inorganic lamellar compound dispersion liquid (1): 1.5 parts
Aqueous solution of 6% by mass of polyvinyl alcohol (CKS50 manufactured by The Nippon Synthetic Chemical Industry Co., Ltd., sulfonic acid-modified, degree of saponification of 99% by mol or higher, degree of polymerization of 300): 0.55 parts
Aqueous solution of 6% by mass of polyvinyl alcohol (PVA-405 manufactured by Kuraray Co., Ltd., degree of saponification of 81.5% by mol, degree of polymerization of 500): 0.03 parts
Aqueous solution of 1% by mass of a surfactant (EMULEX 710) manufactured by Nihon Emulsion Co., Ltd.: 0.86 parts
Ion-exchange water: 6.0 parts
(Preparation of Inorganic Lamellar Compound Dispersion Liquid (1))
Synthetic mica SOMASIF ME-100 (manufactured by Co-op Chemical Co. Ltd.) (6.4 parts) was added to ion-exchange water (193.6 parts) and was dispersed using a homogenizer until the average particle diameter (the laser scattering method) reached 3 μm. The aspect ratio of the obtained dispersed particles was 100 or higher.

II-2. Production of Lithographic Printing Plate Precursor B'-1
A lithographic printing plate precursor B'-1 [for Comparative Example 3] was obtained by being produced in the same manner as the lithographic printing plate precursor B-1 except for the fact that the following photosensitive liquid (2) was prepared instead of the photosensitive liquid (1) and an image-recording layer coating liquid was produced.

<Photosensitive Liquid (2)>
Binder polymer [the above structure]: 0.240 parts
Infrared-absorbing dye [the above structure]: 0.030 parts
Onium salt (polymerization initiator) [the above structure]: 0.162 parts
Polymerizable compound (tris(acryloyloxyethyl)isocyanurate, NK ester A-9300, manufactured by Shin-Nakamura Chemical Co., Ltd.): 0.192 parts
Low-molecular-weight hydrophilic compound (tris(2-hydroxyethyl)isocyanurate): 0.062 parts
Low-molecular-weight hydrophilic compound [the above structure]: 0.050 parts
Sensitization agent (phosphonium compound, the above structure): 0.055 parts
Sensitization agent (benzyl-dimethyl-octylammonium.PF₆ salt): 0.018 parts
Sensitization agent (ammonium group-containing polymer, the above structure, reducing specific viscosity of 44 ml/g): 0.035 parts
Fluorine-based surfactant [the above structure]: 0.008 parts
2-Butanone: 1.091 parts
1-Methoxy-2-propanol: 8.609 parts II-3. Production of Lithographic Printing Plate Precursor B'-2
A lithographic printing plate precursor B'-2 [for Comparative Example 4] was obtained by being produced in the same manner as the lithographic printing plate precursor B-1 except for the fact that the following photosensitive liquid (3) was prepared instead of the photosensitive liquid (1) and an image-recording layer coating liquid was produced.

<Photosensitive Liquid (3)>
Binder polymer [the above structure]: 0.240 parts
Infrared-absorbing dye [the above structure]: 0.030 parts
Comparative compound [the above structure]: 0.060 parts
Onium salt (polymerization initiator) [the above structure]: 0.162 parts
Polymerizable compound (tris(acryloyloxyethyl)isocyanurate, NK ester A-9300, manufactured by Shin-Nakamura Chemical Co., Ltd.): 0.192 parts
Low-molecular-weight hydrophilic compound (tris(2-hydroxyethyl)isocyanurate): 0.062 parts
Low-molecular-weight hydrophilic compound [the above structure]: 0.050 parts Sensitization agent (phosphonium compound, the above structure): 0.055 parts
Sensitization agent (benzyl-dimethyl-octylammonium.$PF_6$ salt): 0.018 parts
Sensitization agent (ammonium group-containing polymer, the above structure, reducing specific viscosity of 44 ml/g): 0.035 parts
Fluorine-based surfactant [the above structure]: 0.008 parts
2-Butanone: 1.091 parts
1-Methoxy-2-propanol: 8.609 parts
II-4. Evaluation of Lithographic Printing Plate Precursors
(i) Color-Developing Properties The obtained lithographic printing plate precursors were exposed using a TRENDSETTER 3244VX manufactured by Creo Co., Ltd. which was equipped with a water-cooling-type 40 W infrared semiconductor laser under conditions of an output of 11.7 W, an external surface drum rotation speed of 250 rpm, and a resolution of 2,400 dpi.

Color development was measured immediately after exposure and two hours after exposure under conditions of a dark plate and room temperature. In addition, the lithographic printing plate precursors were stored for three days under conditions of 60° C. and a humidity of 70% RH, and then color development was measured immediately after the exposure of the lithographic printing plate precursors that had been forcibly aged.

Color development was measured in the same manner as the case of the color developing composition film. A larger value of ΔL indicates superior color-developing properties. The results are shown in Table 2.

(ii) On-Machine Developing Properties

The obtained lithographic printing plate precursors were exposed using a LUXEL PLATESETTER T-6000III manufactured by Fujifilm Corporation which was equipped with an infrared semiconductor laser under conditions of an external surface drum rotation speed of 1,000 rpm, a laser output of 70%, and a resolution of 2,400 dpi. Exposed images were provided with beta images and 50% halftone dot charts of 20 μm dot FM screens.

Without carrying out a development process on the obtained exposed plate precursors, the lithographic printing plate precursors were attached to the plate trunk of a printer LITHRONE 26 manufactured by Komori Corporation. The lithographic printing plate precursors were on-machine-developed using dampening water of ECOLITY-2 (manufactured by Fujifilm Corporation)/tap water=2/98 (capacity ratio) and SPACE COLOR FUSION G(N) BLACK INK (manufactured by DIC Graphics Corporation) by supplying dampening water and ink using the standard automatic printing start method of LITHRONE 26, and then printing was carried out on 100 pieces of TOKUBISHI art paper (manufactured by Mitsubishi Paper Mills Limited) (76.5 kg) at a printing rate of 10,000 pieces per hour.

The on-machine development of non-exposed portions in the image-recording layer on the printer was completed, and the number of pieces of printing paper required until ink was not transferred to the non-image portions was measured as the on-machine developing properties. The results are shown in Table 2.

(iii) Printing Resistance

After the on-machine developing properties immediately after the above-described coating was evaluated, printing was further continued. As the number of printed pieces increased, the image-recording layer gradually wore, and thus the ink concentration on printed matters decreased. The printing resistance was evaluated using the number of printed portions when the value of the halftone dot area ratio of 50% halftone dots in FM screens on printed matters, which was measured using a gretag density meter, decreased to be 5% lower than the measurement value obtained when printing was carried out on $100^{th}$ piece of paper as the number of completely-printed pieces. The results are shown in Table 2.

TABLE 2

| | Lithographic printing plate precursor Type | Specific compound Type | Color developing properties (ΔL) | | | On-machine developing properties (number of pieces) | Printing resistance (ten thousand pieces) |
|---|---|---|---|---|---|---|---|
| | | | Immediately after exposure | After two hours | After forcible exposure | | |
| Example 10 | B-1 | W-1 | 12 | 12 | 12 | 30 | 8 |
| Example 11 | B-2 | W-1 | 12 | 12 | 12 | 30 | 8 |
| Example 12 | B-3 | W-3 | 12 | 12 | 12 | 30 | 8 |
| Example 13 | B-4 | W-4 | 12 | 12 | 12 | 30 | 8 |
| Example 14 | B-5 | W-5 | 12 | 12 | 12 | 30 | 8 |
| Example 15 | B-6 | W-6 | 12 | 12 | 12 | 30 | 8 |
| Example 16 | B-7 | W-8 | 10.5 | 10.5 | 10.5 | 30 | 8 |
| Example 17 | B-8 | W-9 | 10.5 | 10.5 | 10.5 | 30 | 8 |
| Example 18 | B-9 | W-12 | 10 | 10 | 10 | 30 | 8 |
| Comparative Example 3 | B'-1 | — | 4 | 2 | 2 | 30 | 7 |
| Comparative Example 4 | B'-2 | — | 5 | 2.5 | 2.5 | 30 | 8 |

From the results of Table 2, it is clear that, in the lithographic printing plate precursor of the present invention, the printing performance indicated by the on-machine developing properties and the printing resistance and the color-developing properties were excellent, and high color development was maintained even after a certain period of time elapses after exposure and color development. Furthermore, the storage stability is also favorable, and the produced lithographic printing plate precursor can obtain high color development even when exposed after being forcibly aged.

What is claimed is:

1. An infrared-sensitive color developing composition comprising a compound represented by Formula (1), as Component A,

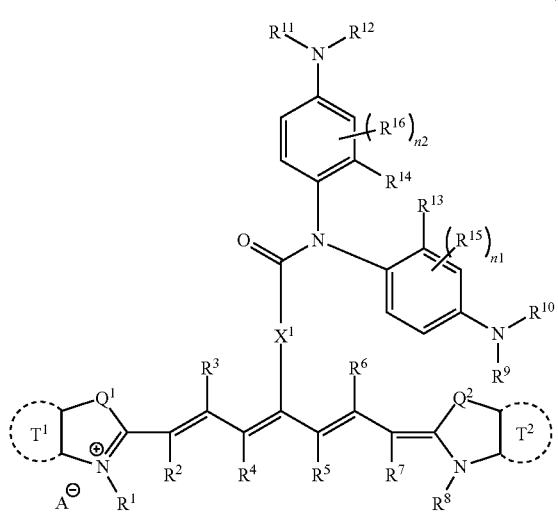

(1)

wherein, in Formula (1), each of $R^1$ and $R^8$ independently represents an alkyl group, each of $R^2$, $R^3$, $R^4$, $R^5$, $R^6$, and $R^7$ independently represents a hydrogen atom or an alkyl group, $R^4$ and $R^5$ may be linked together and thus form a ring, each of $Q^1$ and $Q^2$ independently represents —$NR^0$—, —S—, —O—, or a dialkylmethylene group, $R^0$ represents a hydrogen atom, an alkyl group, or an aryl group, each of $T^1$ and $T^2$ independently represents an aromatic ring or a heterocyclic aromatic ring, $X^1$ represents a divalent linking group, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom or a monovalent substituent, $R^{13}$ and $R^{14}$ may be bonded together and thus form a ring, each of $R^{15}$ and $R^{16}$ independently represents a monovalent substituent, and each of n1 and n2 independently represents an integer of 0 to 3.

2. The infrared-sensitive color developing composition according to claim 1,
wherein the compound represented by Formula (1) is a compound represented by Formula (2) below,

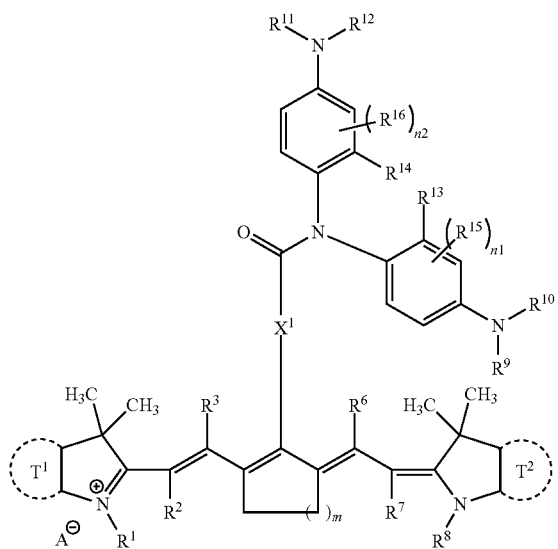

(2)

in Formula (2), each of $R^1$ and $R^8$ independently represents an alkyl group, each of $R^2$, $R^3$, $R^6$, and $R^7$ independently represents a hydrogen atom or an alkyl group, each of $T^1$ and $T^2$ independently represents an aromatic ring or a heterocyclic aromatic ring, $X^1$ represents a group formed by bonding one or more of —O—, —S—, and/or a urethane bond to one or more of divalent hydrocarbon groups, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom, an alkyl group, a halogen atom, $OR^{17}$, $NR^{18}R^{19}$, or $SR^{20}$, $R^{13}$ and $R^{14}$ may form a ring bonded by an alkylene group, —O—, —$NR^{21}$—, —S—, or a group made of a combination of two or more thereof, each of $R^{15}$ and $R^{16}$ independently represents an alkyl group, a halogen atom, $OR^{17}$, $NR^{18}R^{19}$, or $SR^{20}$, each of $R^{17}$, $R^{18}$, $R^{19}$, and $R^{20}$ independently represents an alkyl group or an aryl group, $R^{21}$ represents a hydrogen atom, an alkyl group, or an aryl group, each of n1 and n2 independently represents an integer of 0 to 3, and m represents 1 or 2.

3. The infrared-sensitive color developing composition according to claim 1,
wherein the compound represented by Formula (1) is a compound represented by Formula (3) below,

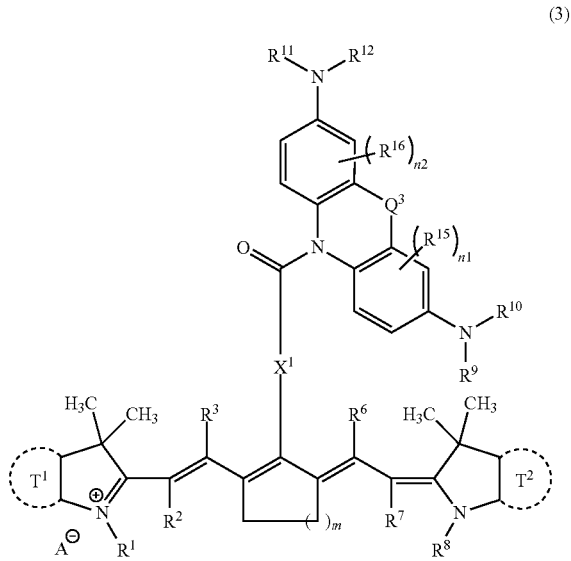

(3)

in Formula (3), each of $R^1$ and $R^8$ independently represents an alkyl group, each of $R^2$, $R^3$, $R^6$, and $R^7$ independently represents a hydrogen atom or an alkyl group, each of $T^1$ and $T^2$ independently represents an aromatic ring or a heterocyclic aromatic ring, $X^1$ represents a group formed by bonding one or more of —O—, —S—, and/or a urethane bond to one or more of divalent hydrocarbon groups, $A^-$ represents a counter anion, each of $R^9$, $R^{10}$, $R^{11}$, and $R^{12}$ independently represents an alkyl group or an aryl group, each of $R^{15}$ and $R^{16}$ independently represents a hydrogen atom, an alkyl group, a halogen atom, $OR^{17}$, $NR^{18}R^{19}$, or $SR^{20}$, each of $R^{17}$, $R^{18}$, $R^{19}$, and $R^{20}$ independently represents an alkyl group or an aryl group, each of n1 and n2 independently represents an integer of 0 to 3, m represents 1 or 2, $Q^3$ represents —O—, —$NR^{22}$—, or —S—, and $R^{22}$ represents an alkyl group or an aryl group.

4. The infrared-sensitive color developing composition according to claim 1, further comprising:
a binder polymer, as Component B.

5. The infrared-sensitive color developing composition according to claim 1, further comprising:
a polymerization initiator, as Component C.

6. The infrared-sensitive color developing composition according to claim 1, further comprising:
a polymerizable compound, as Component D.

7. A lithographic printing plate precursor comprising on a support:
an image-recording layer including a compound represented by Formula (1), as Component A;
a binder polymer, as Component B;
a polymerization initiator, as Component C; and
a polymerizable compound, as Component D,

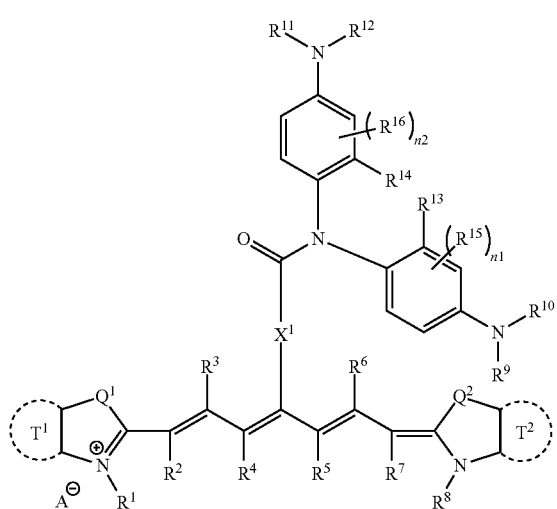

(1)

wherein, in Formula (1), each of $R^1$ and $R^8$ independently represents an alkyl group, each of $R^2$, $R^3$, $R^4$, $R^5$, $R^6$, and $R^7$ independently represents a hydrogen atom or an alkyl group, $R^4$ and $R^5$ may be linked together and thus form a ring, each of $Q^1$ and $Q^2$ independently represents —$NR^0$—, —S—, —O—, or a dialkylmethylene group, $R^0$ represents a hydrogen atom, an alkyl group, or an aryl group, each of $T^1$ and $T^2$ independently represents an aromatic ring or a heterocyclic aromatic ring, $X^1$ represents a divalent linking group, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom or a monovalent substituent, $R^{13}$ and $R^{14}$ may be bonded together and thus form a ring, each of $R^{15}$ and $R^{16}$ independently represents a monovalent substituent, and each of n1 and n2 independently represents an integer of 0 to 3.

8. The lithographic printing plate precursor according to claim 7,
wherein the image-recording layer further contains polymer particles other than Component B.

9. The lithographic printing plate precursor according to claim 7, comprising:
a protective layer on the image-recording layer.

10. The lithographic printing plate precursor according to claim 9,
wherein the protective layer contains an inorganic lamellar compound.

11. A plate making method for a lithographic printing plate, comprising:
a preparation step of preparing the lithographic printing plate precursor according to claim 7;
an exposure step of exposing the lithographic printing plate precursor in an image pattern; and
an on-machine development process step of removing non-image portions by supplying printing ink and dampening water to the lithographic printing plate precursor that has been exposed in an image pattern on a printer.

12. A compound represented by Formula (1),

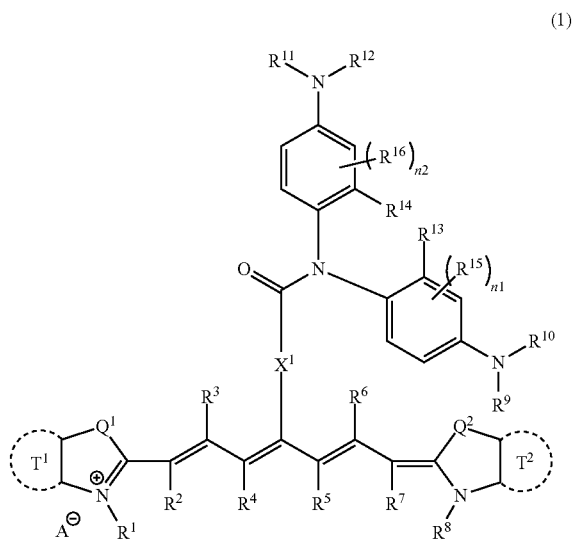

(1)

wherein, in Formula (1), each of $R^1$ and $R^8$ independently represents an alkyl group, each of $R^2$, $R^3$, $R^4$, $R^5$, $R^6$, and $R^7$ independently represents a hydrogen atom or an alkyl group, $R^4$ and $R^5$ may be linked together and thus form a ring, each of $Q^1$ and $Q^2$ independently represents —$NR^0$—, —S—, —O—, or a dialkylmethylene group, $R^0$ represents a hydrogen atom, an alkyl group, or an aryl group, each of $T^1$ and $T^2$ independently represents an aromatic ring or a heterocyclic aromatic ring, $X^1$ represents a divalent linking group, $A^-$ represents a counter anion, each of $R^9$, $R^{10}$, $R^{11}$, and $R^{12}$ independently represents an alkyl group or an aryl group, each of $R^{13}$ and $R^{14}$ independently represents a hydrogen atom or a monovalent substituent, $R^{13}$ and $R^{14}$ may be bonded together and thus form a ring, each of $R^{15}$ and $R^{16}$ independently represents a monovalent substituent, and each of n1 and n2 independently represents an integer of 0 to 3.

13. The compound according to claim 12,
wherein each of $R^1$, $R^8$, $R^9$, $R^{10}$, $R^{11}$, and $R^{12}$ is independently an alkyl group, and $R^2$, $R^3$, $R^6$, and $R^7$ are hydrogen atoms.

14. The compound according to claim 12 which is an infrared-sensitive color developer.

* * * * *